United States Patent
Pickett et al.

(10) Patent No.: US 12,201,387 B2
(45) Date of Patent: Jan. 21, 2025

(54) SYSTEMS AND METHODS FOR TROCAR KINEMATICS

(71) Applicant: Activ Surgical, Inc., Boston, MA (US)

(72) Inventors: Michael Pickett, Boston, MA (US); Vasiliy Buharin, Boston, MA (US); Hossein Dehghani, Boston, MA (US)

(73) Assignee: ACTIV Surgical, Inc., Boston, MA (US)

( * ) Notice: Subject to any disclaimer, the term of this patent is extended or adjusted under 35 U.S.C. 154(b) by 584 days.

(21) Appl. No.: 17/503,108

(22) Filed: Oct. 15, 2021

(65) Prior Publication Data
US 2022/0175471 A1 Jun. 9, 2022

Related U.S. Application Data

(63) Continuation of application No. PCT/US2020/028536, filed on Apr. 16, 2020.
(Continued)

(51) Int. Cl.
*A61B 34/30* (2016.01)
*A61B 17/00* (2006.01)
(Continued)

(52) U.S. Cl.
CPC .......... *A61B 34/30* (2016.02); *A61B 17/3423* (2013.01); *A61B 90/50* (2016.02);
(Continued)

(58) Field of Classification Search
CPC ..... A61B 34/30; A61B 17/3423; A61B 90/50; A61B 2034/2059; A61B 2034/302; A61B 17/34; A61B 34/20
See application file for complete search history.

(56) References Cited

U.S. PATENT DOCUMENTS

| 4,772,831 A | 9/1988 | Casler, Jr. et al. |
| 5,808,665 A | 9/1998 | Green |

(Continued)

FOREIGN PATENT DOCUMENTS

| EP | 2672715 A2 | 12/2013 |
| WO | WO-2010096447 A2 | 8/2010 |

(Continued)

OTHER PUBLICATIONS

Dunn, et al. Laser speckle contrast imaging in biomedical optics. Journal of Biomedical Optics 15(1), 011109 (Jan./Feb. 2010).
(Continued)

*Primary Examiner* — Ian Jen
*Assistant Examiner* — Renee LaRose
(74) *Attorney, Agent, or Firm* — Cesari and McKenna, LLP

(57) ABSTRACT

The present disclosure provides systems and methods for discretizing a movement or a motion of one or more robotic arms. The system may comprise a robotic arm, an end effector coupled to a distal portion of the robotic arm, and a trocar through which the end effector may be inserted. The trocar may comprise a trocar reference point. The system may further comprise a processor configured to (i) determine a starting position and a destination position of a distal end of the end effector, (ii) determine a path between the starting position and the destination position, (iii) determine a plurality of points along the path, and (iv) determine a set of motions to move the distal end of the end effector from the starting position to the destination position, based at least in part on the trocar reference point.

18 Claims, 12 Drawing Sheets

Related U.S. Application Data

(60) Provisional application No. 62/836,201, filed on Apr. 19, 2019.

(51) Int. Cl.
*A61B 17/34* (2006.01)
*A61B 34/20* (2016.01)
*A61B 90/50* (2016.01)

(52) U.S. Cl.
CPC .............. *A61B 2017/00221* (2013.01); *A61B 2034/2059* (2016.02); *A61B 2034/302* (2016.02)

(56) References Cited

U.S. PATENT DOCUMENTS

| | | |
|---|---|---|
| 5,876,325 A | 3/1999 | Mizuno et al. |
| 6,001,108 A | 12/1999 | Wang et al. |
| 6,088,105 A | 7/2000 | Link |
| 6,183,485 B1 | 2/2001 | Thomason et al. |
| 6,206,894 B1 | 3/2001 | Thompson et al. |
| 6,223,100 B1 | 4/2001 | Green |
| 6,309,397 B1 | 10/2001 | Julian et al. |
| 6,325,808 B1 | 12/2001 | Bernard et al. |
| 6,373,963 B1 | 4/2002 | Demers et al. |
| 6,491,702 B2 | 12/2002 | Heilbrun et al. |
| 6,503,195 B1 | 1/2003 | Keller et al. |
| 6,542,249 B1 | 4/2003 | Kofman et al. |
| 6,549,288 B1 | 4/2003 | Migdal et al. |
| 6,563,105 B2 | 5/2003 | Seibel et al. |
| 6,564,086 B2 | 5/2003 | Marchitto et al. |
| 6,613,041 B1 | 9/2003 | Schrunder |
| 6,643,563 B2 | 11/2003 | Hosek et al. |
| 6,645,196 B1 * | 11/2003 | Nixon .................... A61B 34/37 606/1 |
| 6,697,164 B1 | 2/2004 | Babayoff et al. |
| 6,800,057 B2 | 10/2004 | Tsujita et al. |
| 6,850,872 B1 | 2/2005 | Marschner et al. |
| 6,873,867 B2 | 3/2005 | Vilsmeier |
| 6,885,464 B1 | 4/2005 | Pfeiffer et al. |
| RE38,800 E | 9/2005 | Barbour |
| 6,965,690 B2 | 11/2005 | Matsumoto |
| 6,977,732 B2 | 12/2005 | Chen et al. |
| 6,987,531 B2 | 1/2006 | Kamon |
| 7,006,236 B2 | 2/2006 | Tomasi et al. |
| 7,068,825 B2 | 6/2006 | Rubbert et al. |
| 7,092,107 B2 | 8/2006 | Babayoff et al. |
| 7,099,732 B2 | 8/2006 | Geng |
| 7,124,066 B2 | 10/2006 | Marschner et al. |
| 7,152,024 B2 | 12/2006 | Marschner et al. |
| 7,184,150 B2 | 2/2007 | Quadling et al. |
| 7,200,262 B2 | 4/2007 | Sawada |
| 7,224,384 B1 | 5/2007 | Iddan et al. |
| 7,230,725 B2 | 6/2007 | Babayoff et al. |
| 7,242,997 B2 | 7/2007 | Geng |
| 7,305,110 B2 | 12/2007 | Rubbert et al. |
| 7,313,264 B2 | 12/2007 | Crampton |
| 7,319,529 B2 | 1/2008 | Babayoff |
| 7,363,201 B2 | 4/2008 | Marschner et al. |
| 7,385,708 B2 | 6/2008 | Ackerman et al. |
| 7,433,807 B2 | 10/2008 | Marschner et al. |
| 7,435,217 B2 | 10/2008 | Wiklof |
| 7,450,783 B2 | 11/2008 | Talapov et al. |
| 7,477,402 B2 | 1/2009 | Babayoff et al. |
| 7,489,408 B2 | 2/2009 | Harding et al. |
| 7,491,956 B2 | 2/2009 | Knoche et al. |
| 7,492,927 B2 | 2/2009 | Marschner et al. |
| 7,511,829 B2 | 3/2009 | Babayoff |
| 7,522,764 B2 | 4/2009 | Schwotzer |
| 7,577,299 B2 | 8/2009 | Kawamata et al. |
| 7,620,209 B2 | 11/2009 | Stevick et al. |
| 7,630,089 B2 | 12/2009 | Babayoff et al. |
| 7,704,206 B2 | 4/2010 | Suzuki et al. |
| 7,724,378 B2 | 5/2010 | Babayoff |
| 7,724,932 B2 | 5/2010 | Ernst et al. |
| 7,751,871 B2 | 7/2010 | Rubbert |
| 7,763,841 B1 | 7/2010 | McEldowney |
| 7,794,388 B2 | 9/2010 | Draxinger et al. |
| 7,821,649 B2 | 10/2010 | Bendall et al. |
| 7,854,700 B2 | 12/2010 | Orihara |
| 7,898,651 B2 | 3/2011 | Hu et al. |
| 7,944,569 B2 | 5/2011 | Babayoff et al. |
| 7,951,073 B2 | 5/2011 | Freed |
| 7,959,557 B2 | 6/2011 | Weitzner et al. |
| 7,961,912 B2 | 6/2011 | Stevick et al. |
| 7,967,743 B2 | 6/2011 | Ishihara |
| 7,990,548 B2 | 8/2011 | Babayoff et al. |
| 7,995,798 B2 | 8/2011 | Krupnik et al. |
| 8,027,710 B1 | 9/2011 | Dannan |
| 8,038,609 B2 | 10/2011 | Kohno et al. |
| 8,052,636 B2 | 11/2011 | Moll et al. |
| 8,084,753 B2 | 12/2011 | Joshi et al. |
| 8,257,303 B2 | 9/2012 | Moll et al. |
| 8,264,536 B2 | 9/2012 | McEldowney |
| 8,279,418 B2 | 10/2012 | Yee et al. |
| 8,280,152 B2 | 10/2012 | Thiel et al. |
| 8,310,683 B2 | 11/2012 | Babayoff et al. |
| 8,320,621 B2 | 11/2012 | McEldowney |
| 8,326,020 B2 | 12/2012 | Lee et al. |
| 8,330,804 B2 | 12/2012 | Lutian et al. |
| 8,395,342 B2 | 3/2013 | Prisco |
| 8,400,494 B2 | 3/2013 | Zalevsky et al. |
| 8,406,859 B2 | 3/2013 | Zuzak et al. |
| 8,471,897 B2 | 6/2013 | Rodriguez Ramos et al. |
| 8,517,928 B2 | 8/2013 | Orihara |
| 8,553,939 B2 | 10/2013 | Craig et al. |
| 8,558,873 B2 | 10/2013 | McEldowney |
| 8,593,507 B2 | 11/2013 | Yahav |
| 8,610,665 B2 | 12/2013 | Craig et al. |
| 8,617,102 B2 | 12/2013 | Moll et al. |
| 8,649,024 B2 | 2/2014 | Colonna De Lega |
| 8,659,765 B2 | 2/2014 | Ando |
| 8,723,118 B2 | 5/2014 | McEldowney et al. |
| 8,723,923 B2 | 5/2014 | Bloom et al. |
| 8,755,053 B2 | 6/2014 | Fright et al. |
| 8,792,098 B2 | 7/2014 | Dewald et al. |
| 8,803,952 B2 | 8/2014 | Katz et al. |
| 8,823,790 B2 | 9/2014 | Dunn et al. |
| 8,891,087 B2 | 11/2014 | Zuzak et al. |
| 8,896,594 B2 | 11/2014 | Xiong et al. |
| 8,974,378 B2 | 3/2015 | Imaizumi et al. |
| 9,001,190 B2 | 4/2015 | Olivier, III et al. |
| 9,057,784 B2 | 6/2015 | Hudman |
| 9,068,824 B2 | 6/2015 | Findeisen et al. |
| 9,070,194 B2 | 6/2015 | Lee et al. |
| 9,072,445 B2 | 7/2015 | Berguer et al. |
| 9,074,868 B2 | 7/2015 | Bendall et al. |
| 9,089,277 B2 | 7/2015 | Babayoff et al. |
| 9,119,552 B2 | 9/2015 | Baumann et al. |
| 9,135,502 B2 | 9/2015 | Haker et al. |
| 9,142,025 B2 | 9/2015 | Park et al. |
| 9,147,253 B2 | 9/2015 | Yee et al. |
| 9,149,281 B2 | 10/2015 | Bonutti |
| 9,149,348 B2 | 10/2015 | Wu et al. |
| 9,155,544 B2 | 10/2015 | Bonutti |
| 9,157,728 B2 | 10/2015 | Ogawa |
| 9,157,733 B2 | 10/2015 | Dillon et al. |
| 9,186,053 B2 | 11/2015 | Viola |
| 9,192,395 B2 | 11/2015 | Bonutti |
| 9,198,578 B2 | 12/2015 | Zuzak et al. |
| 9,204,952 B2 | 12/2015 | Lampalzer |
| 9,220,570 B2 | 12/2015 | Kim et al. |
| 9,226,645 B2 | 1/2016 | Ntziachristos |
| 9,226,673 B2 | 1/2016 | Ferguson, Jr. et al. |
| 9,226,811 B2 | 1/2016 | Abuzaina |
| 9,247,865 B2 | 2/2016 | Igarashi et al. |
| 9,254,076 B2 | 2/2016 | McDowall |
| 9,254,078 B2 | 2/2016 | McDowall |
| 9,254,103 B2 | 2/2016 | Krishnaswamy et al. |
| 9,261,356 B2 | 2/2016 | Lampert et al. |
| 9,261,358 B2 | 2/2016 | Atiya et al. |
| 9,271,658 B2 | 3/2016 | Ferguson, Jr. et al. |
| 9,274,047 B2 | 3/2016 | Velten et al. |
| 9,282,926 B2 | 3/2016 | Schwotzer et al. |

(56) References Cited

U.S. PATENT DOCUMENTS

| | | |
|---|---|---|
| 9,294,758 B2 | 3/2016 | Xiong et al. |
| 9,297,889 B2 | 3/2016 | Hudman et al. |
| 9,304,603 B2 | 4/2016 | Miller |
| 9,330,464 B1 | 5/2016 | Ackerman et al. |
| 9,345,389 B2 | 5/2016 | Nie et al. |
| 9,345,392 B2 | 5/2016 | Saito |
| 9,345,397 B2 | 5/2016 | Taylor et al. |
| 9,351,643 B2 | 5/2016 | Sharonov |
| 9,364,300 B2 | 6/2016 | Tchouprakov et al. |
| 9,375,844 B2 | 6/2016 | Itkowitz et al. |
| 9,377,295 B2 | 6/2016 | Fright et al. |
| 9,380,224 B2 | 6/2016 | Keskin et al. |
| 9,389,068 B2 | 7/2016 | Ri |
| 9,402,986 B2 | 8/2016 | Bell et al. |
| 9,404,741 B2 | 8/2016 | Schick |
| 9,432,593 B2 | 8/2016 | Yang et al. |
| 9,439,568 B2 | 9/2016 | Atiya et al. |
| 9,443,310 B2 | 9/2016 | Hudman et al. |
| 9,444,981 B2 | 9/2016 | Bellis et al. |
| 9,451,872 B2 | 9/2016 | Yokota |
| 9,457,168 B2 | 10/2016 | Moll et al. |
| 9,462,253 B2 | 10/2016 | Hudman et al. |
| 9,471,864 B2 | 10/2016 | Zatloukal et al. |
| 9,491,441 B2 | 11/2016 | Sarmast et al. |
| 9,494,418 B2 | 11/2016 | Schmidt |
| 9,506,749 B2 | 11/2016 | Bellis et al. |
| 9,513,113 B2 | 12/2016 | Yang et al. |
| 9,513,768 B2 | 12/2016 | Zhao et al. |
| 9,545,220 B2 | 1/2017 | Sidlesky |
| 9,557,574 B2 | 1/2017 | McEldowney |
| 9,581,802 B2 | 2/2017 | Yokota |
| 9,585,600 B2 | 3/2017 | Sharonov |
| 9,615,901 B2 | 4/2017 | Babayoff et al. |
| 9,622,644 B2 | 4/2017 | Yokota |
| 9,622,662 B2 | 4/2017 | Zuzak et al. |
| 9,638,801 B2 | 5/2017 | Boufounos et al. |
| 9,662,018 B2 | 5/2017 | Stopek |
| 9,674,436 B2 | 6/2017 | Crane et al. |
| 9,675,429 B2 | 6/2017 | Lampert et al. |
| 9,690,984 B2 | 6/2017 | Butler et al. |
| 9,696,427 B2 | 7/2017 | Wilson et al. |
| 9,720,506 B2 | 8/2017 | Kim et al. |
| 9,729,860 B2 | 8/2017 | Cohen et al. |
| 9,737,239 B2 | 8/2017 | Kimmel |
| 9,739,594 B2 | 8/2017 | Koerner et al. |
| 9,746,318 B2 | 8/2017 | Sugano |
| 9,752,867 B2 | 9/2017 | Atiya et al. |
| 9,782,056 B2 | 10/2017 | McDowall |
| 9,788,903 B2 | 10/2017 | Kim et al. |
| 9,799,117 B2 | 10/2017 | Chen et al. |
| 9,817,159 B2 | 11/2017 | Hudman |
| 9,821,456 B2 | 11/2017 | Riedel |
| 9,833,145 B2 | 12/2017 | Jeong et al. |
| 9,841,496 B2 | 12/2017 | Hudman |
| 9,844,427 B2 | 12/2017 | Atiya et al. |
| 9,901,409 B2 | 2/2018 | Yang et al. |
| 9,918,640 B2 | 3/2018 | Ntziachristos et al. |
| 9,922,249 B2 | 3/2018 | Kang et al. |
| 9,939,258 B2 | 4/2018 | Lampert et al. |
| 9,943,271 B2 | 4/2018 | Dirauf et al. |
| 9,943,964 B2 | 4/2018 | Hares |
| 9,947,099 B2 | 4/2018 | Bleyer et al. |
| 9,953,428 B2 | 4/2018 | Gren et al. |
| 9,955,140 B2 | 4/2018 | Rhemann et al. |
| 9,955,861 B2 | 5/2018 | Gao et al. |
| 9,958,585 B2 | 5/2018 | Powell et al. |
| 9,958,758 B2 | 5/2018 | Hudman |
| 9,962,244 B2 | 5/2018 | Esbech et al. |
| 9,970,753 B2 | 5/2018 | Han et al. |
| 10,011,014 B2 | 7/2018 | Divoky et al. |
| 10,018,464 B2 | 7/2018 | Boles et al. |
| 10,024,968 B2 | 7/2018 | Hudman et al. |
| 10,039,439 B2 | 8/2018 | Aoyama |
| 10,045,882 B2 | 8/2018 | Balicki et al. |
| 10,055,856 B2 | 8/2018 | Sabater et al. |
| 10,058,256 B2 | 8/2018 | Chen et al. |
| 10,066,997 B2 | 9/2018 | Korner et al. |
| 10,089,737 B2 | 10/2018 | Krieger et al. |
| 10,244,991 B2 | 4/2019 | Shademan et al. |
| 10,390,718 B2 | 8/2019 | Chen et al. |
| 10,398,519 B2 | 9/2019 | Kim et al. |
| 10,675,040 B2 | 6/2020 | Kim et al. |
| 10,722,173 B2 | 7/2020 | Chen et al. |
| 10,792,492 B2 | 10/2020 | Chen et al. |
| 10,948,350 B2 | 3/2021 | Ferguson, Jr. et al. |
| 11,135,028 B2 | 10/2021 | Kim et al. |
| 11,278,220 B2 | 3/2022 | Tucker et al. |
| 2003/0083650 A1 | 5/2003 | Wang et al. |
| 2003/0083651 A1 | 5/2003 | Wang et al. |
| 2003/0195623 A1 | 10/2003 | Marchitto et al. |
| 2004/0073257 A1 | 4/2004 | Spitz |
| 2004/0176751 A1 | 9/2004 | Weitzner et al. |
| 2005/0090840 A1 | 4/2005 | Gerbino et al. |
| 2005/0096515 A1 | 5/2005 | Geng |
| 2006/0020272 A1 | 1/2006 | Gildenberg |
| 2006/0258938 A1 | 11/2006 | Hoffman et al. |
| 2007/0115484 A1 | 5/2007 | Huang et al. |
| 2007/0146719 A1 | 6/2007 | Wedel |
| 2007/0165243 A1 | 7/2007 | Kang et al. |
| 2007/0213749 A1 | 9/2007 | Kogasaka et al. |
| 2007/0232855 A1 | 10/2007 | Weitzner et al. |
| 2007/0239178 A1 | 10/2007 | Weitzner et al. |
| 2007/0249911 A1 | 10/2007 | Simon |
| 2007/0250072 A1 | 10/2007 | Weitzner et al. |
| 2007/0250097 A1 | 10/2007 | Weitzner et al. |
| 2007/0280423 A1 | 12/2007 | Schmidt |
| 2007/0293734 A1 | 12/2007 | Coste-Maniere et al. |
| 2008/0013809 A1 | 1/2008 | Zhu et al. |
| 2008/0107305 A1 | 5/2008 | Vanderkooy et al. |
| 2008/0177281 A1 | 7/2008 | Weitzner et al. |
| 2008/0266391 A1 | 10/2008 | Lee et al. |
| 2009/0221874 A1 | 9/2009 | Vinther et al. |
| 2009/0244260 A1 | 10/2009 | Takahashi et al. |
| 2009/0326324 A1 | 12/2009 | Munoz Martinez et al. |
| 2010/0081875 A1 | 4/2010 | Fowler et al. |
| 2010/0113921 A1 | 5/2010 | Fear et al. |
| 2011/0015518 A1 | 1/2011 | Schmidt et al. |
| 2011/0043609 A1 | 2/2011 | Choi et al. |
| 2011/0057930 A1 | 3/2011 | Keller et al. |
| 2011/0080471 A1 | 4/2011 | Song et al. |
| 2011/0123098 A1 | 5/2011 | Ernst et al. |
| 2011/0202068 A1 | 8/2011 | Diolaiti et al. |
| 2012/0075432 A1 | 3/2012 | Bilbrey et al. |
| 2012/0095354 A1 | 4/2012 | Dunn et al. |
| 2012/0130405 A1 | 5/2012 | Cohn et al. |
| 2012/0165681 A1 | 6/2012 | Keller |
| 2012/0206587 A1 | 8/2012 | Oz et al. |
| 2012/0310098 A1 | 12/2012 | Popovic |
| 2013/0023732 A1 | 1/2013 | Kim et al. |
| 2013/0079928 A1 | 3/2013 | Søe-Knudsen et al. |
| 2013/0085595 A1 | 4/2013 | Kiley et al. |
| 2013/0096576 A1 | 4/2013 | Cooper et al. |
| 2013/0253313 A1 | 9/2013 | Kang et al. |
| 2013/0274596 A1 | 10/2013 | Azizian et al. |
| 2013/0296712 A1 | 11/2013 | Durvasula |
| 2013/0304084 A1 | 11/2013 | Beira et al. |
| 2013/0331644 A1 | 12/2013 | Pandya et al. |
| 2014/0031665 A1 | 1/2014 | Pinto et al. |
| 2014/0052005 A1 | 2/2014 | Yokota |
| 2014/0092281 A1 | 4/2014 | Nisenzon et al. |
| 2014/0148816 A1 | 5/2014 | McDonald et al. |
| 2014/0148819 A1 | 5/2014 | Inoue et al. |
| 2014/0194747 A1 | 7/2014 | Kruglick et al. |
| 2014/0243850 A1 | 8/2014 | Sadaka |
| 2014/0257329 A1 | 9/2014 | Jang et al. |
| 2014/0277741 A1 | 9/2014 | Kwon et al. |
| 2015/0012016 A1 | 1/2015 | Stone |
| 2015/0164329 A1 | 6/2015 | Schmidt et al. |
| 2015/0238276 A1 | 8/2015 | Atarot et al. |
| 2015/0266183 A1 | 9/2015 | Alifragkis et al. |
| 2015/0377613 A1 | 12/2015 | Small et al. |
| 2016/0128553 A1 | 5/2016 | Geng |
| 2016/0136805 A1 | 5/2016 | Soe-Knudsen et al. |
| 2016/0139039 A1 | 5/2016 | Ikehara et al. |

(56) References Cited

U.S. PATENT DOCUMENTS

| | | |
|---|---|---|
| 2016/0157942 A1 | 6/2016 | Gombert et al. |
| 2016/0206391 A1 | 7/2016 | Deodhar |
| 2016/0239978 A1 | 8/2016 | Cole et al. |
| 2016/0260206 A1 | 9/2016 | Jung et al. |
| 2016/0262615 A1 | 9/2016 | Jung et al. |
| 2016/0278678 A1 | 9/2016 | Valdes et al. |
| 2016/0296225 A1 | 10/2016 | Rohl et al. |
| 2016/0300348 A1 | 10/2016 | Nadeau et al. |
| 2016/0307325 A1 | 10/2016 | Wang et al. |
| 2016/0307326 A1 | 10/2016 | Wang |
| 2016/0309068 A1 | 10/2016 | Nadeau et al. |
| 2016/0335472 A1 | 11/2016 | Lee et al. |
| 2016/0346930 A1 | 12/2016 | Hares |
| 2017/0014030 A1 | 1/2017 | Rentschler et al. |
| 2017/0020393 A1 | 1/2017 | Rentschler et al. |
| 2017/0020615 A1 | 1/2017 | Koenig et al. |
| 2017/0026633 A1 | 1/2017 | Riza |
| 2017/0030710 A1 | 2/2017 | Rentschler et al. |
| 2017/0032531 A1 | 2/2017 | Nagata et al. |
| 2017/0059305 A1 | 3/2017 | Nonn et al. |
| 2017/0079724 A1 | 3/2017 | Yang et al. |
| 2017/0100024 A1 | 4/2017 | Shahmoon et al. |
| 2017/0112368 A1 | 4/2017 | Stern et al. |
| 2017/0143237 A1 | 5/2017 | Yokota |
| 2017/0164836 A1 | 6/2017 | Krishnaswamy et al. |
| 2017/0172382 A1 | 6/2017 | Nir et al. |
| 2017/0172384 A1 | 6/2017 | Yokota |
| 2017/0209031 A1 | 7/2017 | Nakamura et al. |
| 2017/0227942 A1 | 8/2017 | Thomson et al. |
| 2017/0228879 A1 | 8/2017 | Sato |
| 2017/0251900 A1 | 9/2017 | Hansen et al. |
| 2017/0280970 A1 | 10/2017 | Sartor et al. |
| 2017/0328704 A1 | 11/2017 | Atiya et al. |
| 2017/0333030 A1 | 11/2017 | Bourland, III et al. |
| 2017/0347043 A1 | 11/2017 | Rephaeli et al. |
| 2017/0366773 A1 | 12/2017 | Kiraly et al. |
| 2018/0003943 A1 | 1/2018 | Chan |
| 2018/0008371 A1 | 1/2018 | Manus |
| 2018/0042466 A1 | 2/2018 | Kang et al. |
| 2018/0047165 A1 | 2/2018 | Sato |
| 2018/0104009 A1 | 4/2018 | Abhari et al. |
| 2018/0125586 A1 | 5/2018 | Sela et al. |
| 2018/0165823 A1 | 6/2018 | Ludwig |
| 2018/0174318 A1 | 6/2018 | Wang et al. |
| 2018/0214241 A1 | 8/2018 | Furuta et al. |
| 2018/0235715 A1 | 8/2018 | Amiot et al. |
| 2018/0243043 A1 | 8/2018 | Michihata et al. |
| 2018/0338806 A1 | 11/2018 | Grubbs |
| 2018/0345492 A1 | 12/2018 | Watanabe et al. |
| 2020/0305721 A1 | 10/2020 | Chen et al. |
| 2021/0030277 A1 | 2/2021 | Ferguson, Jr. et al. |
| 2021/0137611 A1* | 5/2021 | Traina ............. A61B 17/3423 |
| 2021/0282654 A1 | 9/2021 | Cha et al. |
| 2021/0354285 A1 | 11/2021 | Buharin et al. |
| 2022/0000557 A1 | 1/2022 | Dehghani |
| 2022/0015844 A1 | 1/2022 | Dehghani |
| 2022/0020160 A1 | 1/2022 | Buharin |

FOREIGN PATENT DOCUMENTS

| | | |
|---|---|---|
| WO | WO-2010096453 A1 | 8/2010 |
| WO | WO-2012096878 A2 | 7/2012 |
| WO | WO-2014152753 A1 | 9/2014 |
| WO | WO-2015070010 A1 | 5/2015 |
| WO | WO-2016061052 A1 | 4/2016 |
| WO | WO-2016153741 A1 | 9/2016 |
| WO | WO-2017075602 A1 | 5/2017 |
| WO | WO-2018067515 A1 | 4/2018 |
| WO | WO-2019045971 A1 | 3/2019 |
| WO | WO-2020006454 A1 | 1/2020 |
| WO | WO-2020118244 A1 | 6/2020 |
| WO | WO-2020140042 | 7/2020 |
| WO | WO-2020140048 A1 | 7/2020 |
| WO | WO-2020140056 | 7/2020 |
| WO | WO-2020214821 | 11/2020 |
| WO | WO-2022029308 A1 | 2/2022 |
| WO | WO-2022058499 A1 | 3/2022 |

OTHER PUBLICATIONS

EP19901561.1 Extended European Search Report dated Jan. 4, 2023.

EP19902562.8 Extended Search Report dated Aug. 22, 2022.

Holstein-Rathlou et al. Nephron blood flow dynamics measured by laser speckle contrast imaging. Am J Phsiol Renal Physiol 300: F319-F329, 2011.

PCT/US19/068756 Search Report & Written Opinion dated Apr. 1, 2020.

PCT/US19/068765 Search Report & Written Opinion dated Apr. 1, 2020.

PCT/US19/068778 Search Report & Written Opinion dated Apr. 1, 2020.

PCT/US19/65056 International Search Report and Written Opinion dated Nov. 6, 2020.

PCT/US20/28536 Search Report & Written Opinion dated Jul. 21, 2020.

Richards et al. Intraoperative laser speckle contrast imaging with retrospective motion correction for quantitative assessment of cerebral blood flow. Neurophotonics 1(1), 015006 (Jul.-Sep. 2014).

Richards et al. Low-cost laser speckle contrast imaging of blood flow using a webcam. 2013 Optical Society of America.

U.S. Appl. No. 17/338,030 Office Action dated Oct. 4, 2023.

* cited by examiner

SYSTEMS AND METHODS FOR TROCAR KINEMATICS

CROSS-REFERENCE

This application is a continuation application of International Application No. PCT/US2020/028536, filed on Apr. 16, 2020, which application claims priority from U.S. Provisional Patent Application No. 62/836,201 filed on Apr. 19, 2019, which applications are incorporated herein by reference in their entirety for all purposes.

BACKGROUND

Robotic surgery, or robot-assisted surgery, may allow doctors to perform many types of complex procedures with more precision, flexibility and control than is possible with conventional surgical techniques. Robotic surgery may be used for minimally invasive surgical procedures performed through tiny incisions in a subject's body.

SUMMARY

The precision, flexibility, and control of robotic surgical systems and methods may be enhanced through accurate detection and tracking of the positions and orientations of different robotic subsystems (e.g., robotic arms and/or end effectors). The positions and orientations of robotic arms and end effectors may change continuously during a surgical procedure. Surgical operators may benefit from a robotic surgical system that can use various reference points to accurately track the positions and orientations of medical tools or instruments attachable to such robotic arms and end effectors to determine one or more optimal motion paths for the robotic arms and end effectors through a surgical scene. The one or more optimal motion paths may allow a surgical operator to accurately and reliably position and/or orient one or more medical tools or instruments at or near a region of interest within a surgical scene.

Embodiments of the present disclosure generally relate to trocar kinematics. In one aspect, the present disclosure describes the discretizing motion of a distal end of an end effector between two points in a robotic surgical system.

In another aspect, the present disclosure provides systems and methods for determining a translation and/or a rotation of an end effector during motion through a trocar. In some embodiments, the system may comprise a first robotic arm having a proximal end and a distal end, where the proximal end is fixed to a base. An end effector may be disposed at the distal end of the robotic arm, where the end effector has a proximal end and a distal end. The end effector may be disposed within the trocar. The system may further comprise a computing node comprising a computer readable storage medium having program instructions embodied therewith, which program instructions may be executable by a processor of the computing node to cause the processor to perform a method for determining a three-dimensional starting position and a three-dimensional destination position of the distal end of the end effector. In some embodiments, the processor may be configured to determine a path between the starting position and the destination position. In some embodiments, the processor may be configured to determine a plurality of points along the path. In some embodiments, the processor may be configured to determine a projected vector from a trocar reference point to a first point of the plurality of points. In some embodiments, the processor may be configured to determine an in-plane rotation of the end effector such that the trocar reference point is maintained. In some embodiments, the processor may be configured to determine a rotation and/or a translation of the end effector based at least in part on the starting position, the first point of the plurality of points, and the in-plane rotation.

In another aspect, the present disclosure provides a method for determining a translation and/or a rotation of an end effector during motion through a trocar. The method may comprise providing a robotic arm having a proximal and distal end. The robotic arm may include an end effector disposed at the distal end, where the end effector has a proximal end and a distal end. The end effector may be disposed within the trocar. In some embodiments, the method may comprise determining a three-dimensional starting position and a three-dimensional destination position of the distal end of the end effector. In some embodiments, the method may comprise determining a path between the starting position and the destination position. In some embodiments, the method may comprise determining a plurality of points along the path. In some embodiments, the method may comprise determining a projected vector from a trocar reference point to a first point of the plurality of points. In some embodiments, the method may comprise determining an in-plane rotation of the end effector such that the trocar reference point is maintained. In some embodiments, the method may comprise determining a rotation and translation of the end effector based at least in part on the starting position, the first point of the plurality of points, and the in-plane rotation.

In another aspect, the present disclosure provides a computer program product for determining a translation and/or a rotation of an end effector during motion through a trocar, in the form of a computer readable storage medium having program instructions embodied therewith. The program instructions may be executable by a processor to cause the processor to perform a method for determining a three-dimensional starting position and a three-dimensional destination position of a distal end of an end effector. The end effector may be disposed at a distal end of a robotic arm. In some embodiments, the processor may be configured to determine a path between the starting position and the destination position. In some embodiments, the processor may be configured to determine a plurality of points along the path. In some embodiments, the processor may be configured to determine a projected vector from a trocar reference point to a first of the plurality of points. In some embodiments, the processor may be configured to determine an in-plane rotation of the end effector such that the trocar reference point is maintained. In some embodiments, the processor may be configured to determine a rotation and translation of the end effector based at least in part on the starting position, the first point of the plurality of points, and the in-plane rotation.

In another aspect, the present disclosure provides a system for moving an end effector. The system may comprise a robotic arm; an end effector coupled to a distal portion of the robotic arm; a trocar through which the end effector is configured to be inserted, wherein the trocar comprises a trocar reference point; and a processor configured to (i) determine a starting position and a destination position of a distal end of the end effector, (ii) determine a path between the starting position and the destination position, (iii) determine a plurality of points along the path, and (iv) determine a set of motions to move the distal end of the end effector from the starting position to the destination position, based at least in part on the trocar reference point.

In some embodiments, the processor may be further configured to determine a projected vector from the trocar reference point to a first point of the plurality of points. In some embodiments, the processor may be further configured to determine an in-plane rotation of the end effector such that the trocar reference point is maintained during the in-plane rotation. In some embodiments, the processor may be further configured to determine one or more rotations and one or more translations of the end effector to move the distal end of the end effector to the destination position, based at least in part on the starting position, the first point of the plurality of points, and the in-plane rotation of the end effector.

In some embodiments, the trocar reference point may correspond to a reference point that is located on the trocar. In some embodiments, the reference point may correspond to a portion of the trocar that is located adjacent to an incision in a subject's body.

In some embodiments, the processor may be configured to use the trocar reference point to compute a reference frame of the end effector. In some embodiments, the processor may be configured to use the trocar reference point to compute a relative position and a relative orientation of the end effector.

In some embodiments, the set of motions may be configured to adjust the position and the orientation of the distal end of the end effector to enable a medical operator to access one or more portions of a surgical scene while avoiding one or more obstacles in the surgical scene. In some embodiments, the set of motions may be configured to adjust the position and the orientation of the distal end of the end effector to enable a medical operator to perform one or more steps of a surgical procedure while minimizing damage to a subject.

In some embodiments, the in-plane rotation may be determined based at least in part on a rotation matrix, wherein the rotation matrix is computed as a function of (i) a trocar z-axis vector and (ii) the projected vector. In some embodiments, the rotation matrix may comprise a rotation portion corresponding to a rotational motion of the end effector and a translation portion corresponding to a translational motion of the end effector. In some embodiments, the rotation matrix may comprise an N×N matrix, wherein N is an integer greater than or equal to 3. In some embodiments, the rotation matrix may comprise a 4×4 matrix.

In some embodiments, the in-plane rotation may be determined based at least in part on an angle between the end effector and the projected vector. In some embodiments, the angle between the end effector and the projected vector may range between 0 degrees and about 45 degrees. In some embodiments, the angle may be greater than or equal to 45 degrees.

In some embodiments, the plurality of points along the path may be determined by discretizing the path into a plurality of segments having one or more predetermined lengths. In some embodiments, the plurality of segments may comprise a first set of segments with a same length and a second set of segments with different lengths. In some embodiments, the one or more predetermined lengths may be different lengths. In some embodiments, the one or more predetermined lengths may be a same length. In some embodiments, the path may comprise a linear portion defined by a vector. In some embodiments, the path may comprise a curved portion defined by a plurality of vectors.

In some embodiments, the processor may be further configured to determine a set of transformations for the one or more rotations and the one or more translations of the end effector from a first reference frame to a second reference frame. In some embodiments, the first reference frame may be a frame of reference defined relative to the end effector and the second reference frame may be a frame of reference defined relative to the robotic arm.

In another aspect, the present disclosure provides a method for moving an end effector. The method may comprise: (a) providing (i) a robotic arm, wherein the robotic arm comprises the end effector, (ii) a trocar through which the end effector is configured to be inserted, wherein the trocar comprises a trocar reference point, and (iii) a processor; and (b) using the processor to (i) determine a starting position and a destination position of a distal end of the end effector, (ii) compute a path between the starting position and the destination position, (iii) identify a plurality of points along the path, and (iv) generate a set of motions to move the distal end of the end effector from the starting position to the destination position, based at least in part on the trocar reference point. In some embodiments, the end effector may be coupled to a distal portion of the robotic arm.

In some embodiments, the trocar reference point may correspond to a reference point that is located on the trocar. In some embodiments, the reference point may correspond to a portion of the trocar that is located adjacent to an incision in a subject's body.

In some embodiments, the method may further comprise using the trocar reference point to compute a reference frame of the end effector. In some embodiments, the method may further comprise using the trocar reference point to compute a relative position and a relative orientation of the end effector. In some embodiments, the method may further comprise using the set of motions to adjust the position and the orientation of the distal end of the end effector to enable a medical operator to access one or more portions of a surgical scene while avoiding one or more obstacles in the surgical scene. In some embodiments, the method may further comprise using the set of motions to adjust the position and the orientation of the distal end of the end effector to enable a medical operator to perform one or more steps of a surgical procedure while minimizing damage to a subject.

In some embodiments, the method may further comprise determining a projected vector from the trocar reference point to a first point of the plurality of points. In some embodiments, the method may further comprise determining an in-plane rotation of the end effector such that the trocar reference point is maintained during the in-plane rotation. In some embodiments, the method may further comprise determining one or more rotations and one or more translations of the end effector to move the distal end of the end effector to the destination position, based at least in part on the starting position, the first point of the plurality of points, and the in-plane rotation of the end effector.

In some embodiments, the in-plane rotation may be determined based at least in part on a rotation matrix, wherein the rotation matrix is computed as a function of (i) a trocar z-axis vector and (ii) the projected vector. In some embodiments, the rotation matrix may comprise a rotation portion corresponding to a rotational motion of the end effector and a translation portion corresponding to a translational motion of the end effector. In some embodiments, the rotation matrix may comprise an N×N matrix, wherein N is an integer greater than or equal to 3. In some embodiments, the rotation matrix may comprise a 4×4 matrix.

In some embodiments, the in-plane rotation may be determined based at least in part on an angle between the end effector and the projected vector. In some embodiments, the angle between the end effector and the projected vector may range between 0 degrees and about 45 degrees. In some embodiments, the angle may be greater than or equal to 45 degrees.

In some embodiments, the plurality of points along the path may be determined by discretizing the path into a plurality of segments having one or more predetermined lengths. In some embodiments, the plurality of segments may comprise a first set of segments with a same length and a second set of segments with different lengths. In some embodiments, the one or more predetermined lengths may be different lengths. In some embodiments, the one or more predetermined lengths may be a same length. In some embodiments, the path may comprise a linear portion defined by a vector. In some embodiments, the path may comprise a curved portion defined by a plurality of vectors.

In some embodiments, the method may further comprise determining a set of transformations for the one or more rotations and the one or more translations of the end effector from a first reference frame to a second reference frame. In some embodiments, the first reference frame may be a frame of reference defined relative to the end effector and the second reference frame may be a frame of reference defined relative to the robotic arm.

In another aspect, the present disclosure provides a computer program comprising a computer readable storage medium having program instructions embodied therewith, the program instructions executable by a processor to cause the processor to perform a method for moving an end effector. The method may comprise: (a) determining a starting position and a destination position of a distal end of the end effector; (b) computing a path between the starting position and the destination position; (c) identifying a plurality of points along the path; and (d) generating a set of motions to move the distal end of the end effector from the starting position to the destination position, based at least in part on a trocar reference point. In some embodiments, the end effector may be coupled to a distal portion of a robotic arm In some embodiments, the trocar reference point may correspond to a reference point that is located on a trocar through which the end effector is inserted. In some embodiments, the reference point may correspond to a portion of the trocar that is located adjacent to an incision in a subject's body.

In some embodiments, the method may further comprise using the trocar reference point to compute a reference frame of the end effector. In some embodiments, the method may further comprise using the trocar reference point to compute a relative position and a relative orientation of the end effector. In some embodiments, the method may further comprise using the set of motions to adjust the position and the orientation of the distal end of the end effector to enable a medical operator to access one or more portions of a surgical scene while avoiding one or more obstacles in the surgical scene. In some embodiments, the method may further comprise using the set of motions to adjust the position and the orientation of the distal end of the end effector to enable a medical operator to perform one or more steps of a surgical procedure while minimizing damage to a subject. In some embodiments, the method may further comprise determining a projected vector from the trocar reference point to a first point of the plurality of points.

In some embodiments, the method may further comprise determining an in-plane rotation of the end effector such that the trocar reference point is maintained during the in-plane rotation. In some embodiments, the method may further comprise determining one or more rotations and one or more translations of the end effector to move the distal end of the end effector to the destination position, based at least in part on the starting position, the first point of the plurality of points, and the in-plane rotation of the end effector. In some embodiments, the in-plane rotation may be determined based at least in part on a rotation matrix, wherein the rotation matrix is computed as a function of (i) a trocar z-axis vector and (ii) the projected vector.

In some embodiments, the rotation matrix may comprise a rotation portion corresponding to a rotational motion of the end effector and a translation portion corresponding to a translational motion of the end effector. In some embodiments, the rotation matrix may comprise an N×N matrix, wherein N is an integer greater than or equal to 3. In some embodiments, the rotation matrix may comprise a 4×4 matrix. In some embodiments, the in-plane rotation may be determined based at least in part on an angle between the end effector and the projected vector. In some embodiments, the angle between the end effector and the projected vector may range between 0 degrees and about 45 degrees. In some embodiments, the angle may be greater than or equal to 45 degrees.

In some embodiments, the plurality of points along the path may be determined by discretizing the path into a plurality of segments having one or more predetermined lengths. In some embodiments, the plurality of segments may comprise a first set of segments with a same length and a second set of segments with different lengths. In some embodiments, the one or more predetermined lengths may be different lengths. In some embodiments, the one or more predetermined lengths may be a same length. In some embodiments, the path may comprise a linear portion defined by a vector. In some embodiments, the path may comprise a curved portion defined by a plurality of vectors.

In some embodiments, the method may further comprise determining a set of transformations for the one or more rotations and the one or more translations of the end effector from a first reference frame to a second reference frame. In some embodiments, the first reference frame may be a frame of reference defined relative to the end effector and the second reference frame may be a frame of reference defined relative to the robotic arm.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
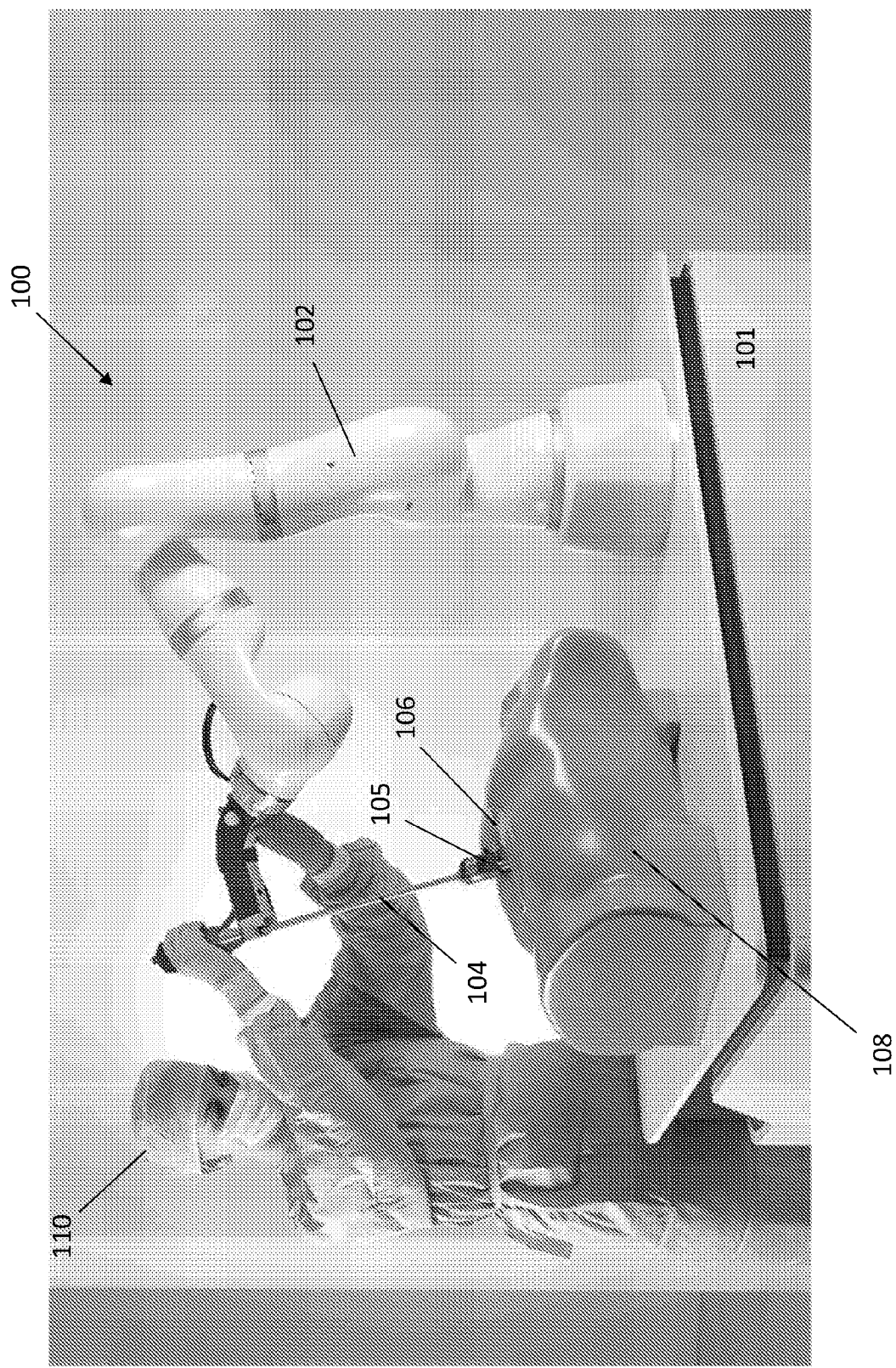
FIG. 1 schematically illustrates a robotic arm system for performing laparoscopic surgery, in accordance with some embodiments.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Whenever the term "at least," "greater than" or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

Trocar Kinematics

Many surgical maneuvers (e.g., suturing, cutting, and/or folding) require highly dexterous and highly accurate motion of surgical tools to achieve a satisfactory surgical outcome. In fully automated robotic surgical procedures, surgical robots generally include an end effector tool that is inserted through a trocar that was previously inserted into a small, keyhole incision in a body. The end effector may include any suitable medical tool, such as, for example, a camera, a cutting tool, a gripping tool, a crimping tool, an electrocautery tool, or any other medical tool or surgical instrument that is usable to perform or aid in a performance of one or more steps of a surgical procedure. When the end effector is inserted through the trocar in the keyhole incision, the location of the distal end of the end effector and its orientation may be unknown to a surgeon. During robotic surgeries, the end effector may change positions and/or orientations relative to a surgical site (e.g., within an abdominal cavity). In such cases, when a surgical operator desires to adjust a position and/or an orientation of an end effector to visualize different portions of a surgical scene or to perform one or more surgical operations within the surgical scene, the surgical operator may need to determine a motion path between the starting position of the end effector and the destination of the end effector. In some cases, the end effector may be inserted through a trocar that is within a keyhole incision in a subject's body. In such cases, when a surgical operator moves the end effector tool within the subject's body, the end effector may pivot about a reference point at the keyhole incision. In some cases, the end effector may pivot relative to the trocar to prevent any injury or damage to a tissue region at or near the keyhole incision in the patient's body (e.g., tearing or other injury at or near the keyhole incision). A frame of reference corresponding to a position and/or an orientation of the trocar may be determined and used to compute one or more optimal motion paths of the end effector. In some cases, the frame of reference corresponding to the position and/or the orientation of the trocar may be determined and used to verify that the trocar is properly positioned during the surgery to minimize damage to one or more tissue regions at or near the keyhole incision. In some cases, one or more optimal motion paths of the end effector may be computed such that the trocar does not interfere with various bodily structures during a surgical procedure, which is critically important to the surgical procedure since the end effector may be configured and/or controlled by a surgical operator to perform complex maneuvers in a small space within a surgical site. The orientation of the trocar may be determined or computed by discretizing one or more motion paths (e.g., curved or linear) between a starting position and a destination position.

In some embodiments, a robotic arm of a robotic surgical system may be configured to pivot around a predefined fixed point during a surgical procedure. In some embodiments, these predefined fixed points may be on a trocar of the robotic arm such that the robotic arm pivots around the trocar. In some embodiments, the robotic arm may comprise a separate motorized track that extends a medical tool or instrument through the trocar. In some embodiments, the robotic arm may not comprise the separate motorized track. In cases where the robotic arm comprises a separate motorized track, the pivoting of the robotic arm may be decoupled from the extension of the medical tool or instrument. In some embodiments, where the medical tool or instrument is affixed to the end of the trocar without a separate motorized track, a system and method for determining the pivoting and extending motions is needed to accurately and reliably maneuver the tool as needed while minimizing damage to one or more tissue regions or critical structures in or near the surgical site.

Accordingly, a need exists for systems and methods for determining the rotation and translation of a trocar by iterating over discretized path segments (e.g., linear and/or curved) to enable accurate surgical maneuvers and improve robotic-assisted surgery.

FIG. 1 illustrates a robotic arm system 100 for performing laparoscopic surgery according to an embodiment of the present disclosure. The robotic arm system 100 may comprise a robotic arm 102 affixed to a base 101 at a proximal end. The robotic arm 102 may further comprise an end effector 104 at the distal end of the robotic arm 102. The end effector 104 may be inserted through a trocar 105 that was previously inserted through a keyhole incision 106 in the abdomen 108 by a healthcare provider 110 overseeing the robotic surgery.

Figure 2:
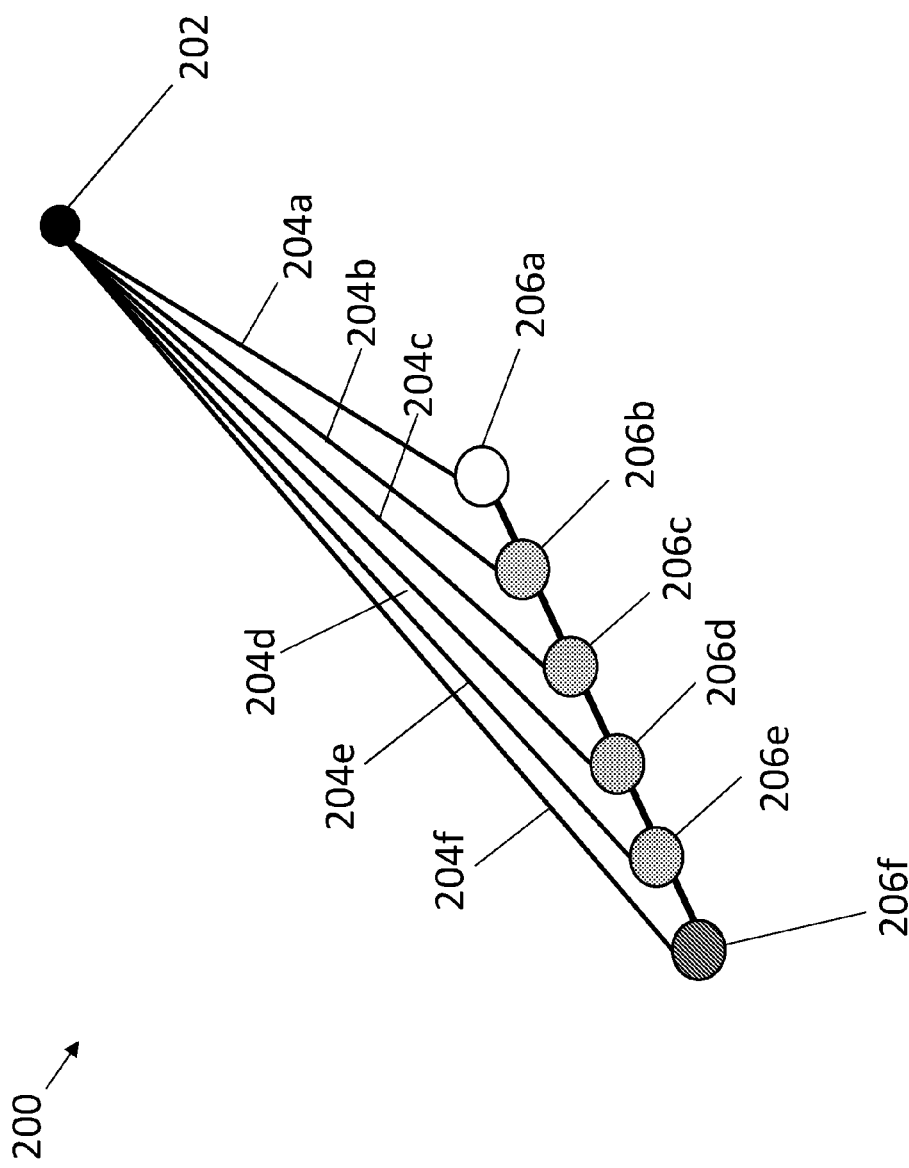
FIG. 2 schematically illustrates a discretized linear path of a distal end of an end effector, in accordance with some embodiments.

FIG. 2 illustrates a discretized path 200 of a distal end of an end effector according to embodiments of the present disclosure. The end effector may be similar to the end effector described above with respect to FIG. 1. A reference point 202 on the trocar may be used to compute the reference frame of the end effector including the three-dimensional position (e.g., x, y, z) and/or the Euler angles (e.g., $\alpha$, $\beta$, $\gamma$) of the end effector shaft. In some embodiments, the reference point may be stationary. In some embodiments, the reference point may correspond to a point on the trocar that is at the keyhole incision. A motion path 200 of a distal end of an end effector may comprise a starting point 206a and a destination point 206f. The motion path between the starting point 206a and the destination point 206f may be discretized to include additional points 206b-206e. FIG. 2 further illustrates projections 204a-204f that may correspond to a projection of the end effector shaft from the trocar reference point 202 to the distal end of the end effector at each point 206a-206f along the motion path 200. In various embodiments, as the distal end of the end effector moves along the path 300, the end effector shaft may pass through the reference point 302 at each incremental step. In various embodiments, the path may be discretized into any suitable number of points. The number of points may be at least about 1, 2, 3, 4, 5, 6, 7, 8, 9, 10, 20, 30, 40, 50, 60, 70, 80, 90, 100, or more. In various embodiments, a larger number of points may permit a higher level of precision and/or a higher resolution of motion. Projections of the end effector at each point 206a-206f along the discretized path may pass through the trocar reference point 202.

In various embodiments, as illustrated in FIG. 2, the path 200 of the distal end of the end effector may be linear. In various embodiments, a vector may be computed using the starting position and the destination position of the end effector. In various embodiments, the vector may be discretized into two or more points in three-dimensional space that are parameterized increments along the vector (e.g., 2 mm increments). In various embodiments, the discretized path may include a path segment between each adjacent pair of points 206a-206j. The points along the path may be used to iteratively determine a reference frame (x, y, z, $\alpha$, $\beta$, $\gamma$) that takes the end effector shaft through the trocar reference point.

Figure 3:
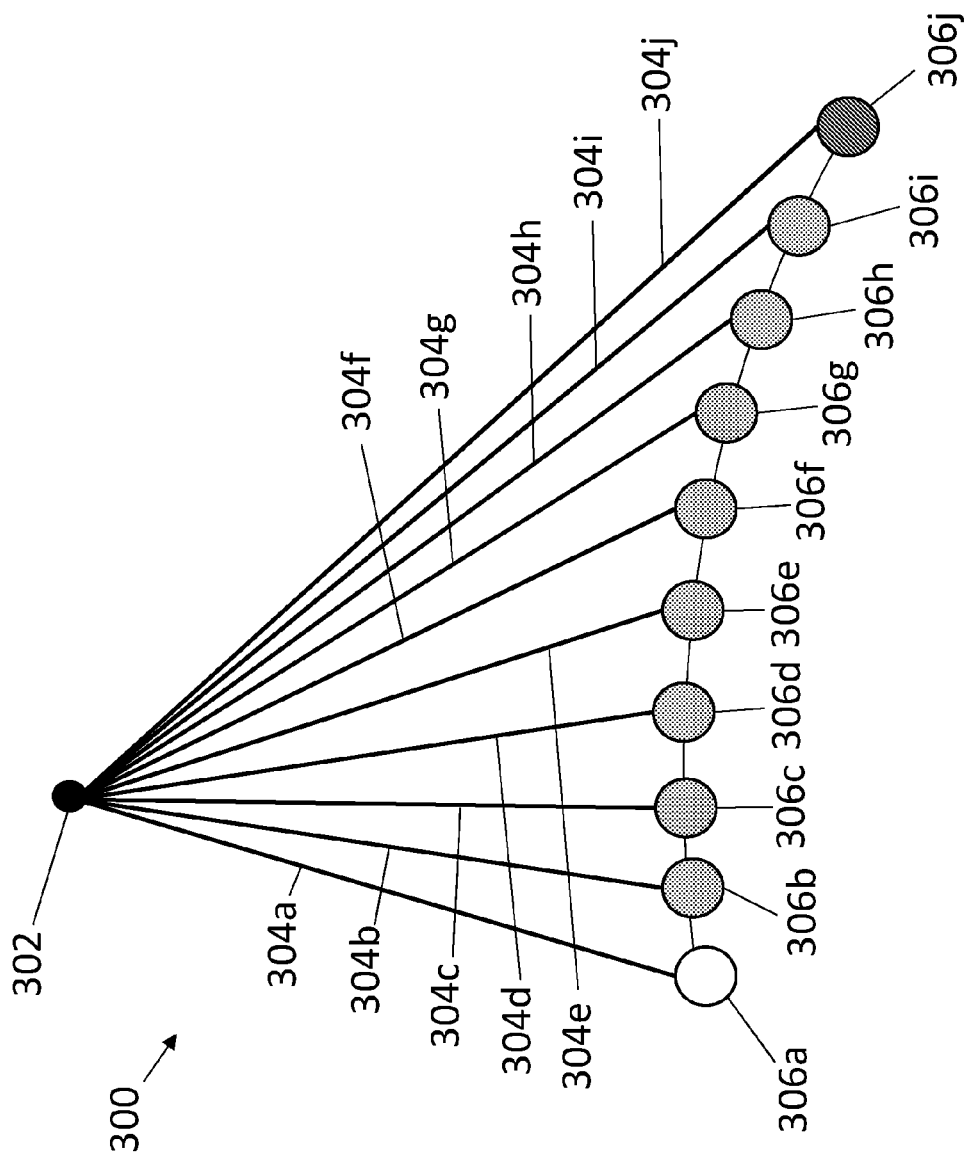
FIG. 3 schematically illustrates a discretized curved path of a distal end of an end effector, in accordance with some embodiments.

FIG. 3 illustrates a discretized path 300 of a distal end of an end effector according to embodiments of the present disclosure. The end effector may be similar to the end effector described above with respect to FIG. 1. A reference point 302 on the trocar may be used to compute the reference frame of the end effector including the three-dimensional position (x, y, z) and the Euler angles ($\alpha$, $\beta$, $\gamma$) of the end effector shaft. In various embodiments, the reference point may be stationary. In various embodiments, the reference point may correspond to a point on the trocar that is at or near the keyhole incision. In various embodiments, as the distal end of the end effector moves along the discretized motion path 300, the end effector shaft may pass through the reference point 302 at each incremental step of the distal end of the end effector represented by points 306a-306j. The discretized motion path 300 of the distal end of the end effector may comprise a starting point 306a and a destination point 306j. The path between the starting point 306a and the destination point 306j may be discretized into additional points 306b-306i. FIG. 3 further illustrates projections 304a-304j that represent the projection of the end effector shaft from the trocar reference point 302 to the distal end of the end effector at each point 306a-306j along the path 300. In various embodiments, the path may be discretized into any suitable number of points. In various embodiments, a larger number of points may permit a higher level of precision and/or a higher resolution of motion. Projections of the end effector at each point 306a-306j along the discretized path may pass through the trocar reference point 302.

In various embodiments, as illustrated in FIG. 3, the path 300 of the distal end of the end effector may be non-linear (e.g., curved). In various embodiments, the path may be computed using the starting position and the destination position of the end effector. In various embodiments, the path may be discretized into two or more points in three-dimensional space that are parameterized increments along the vector (e.g., 2 mm increments). In various embodiments, the discretized path may comprise a path segment between each adjacent pair of points 306a-306j. The points along the path may be used to iteratively determine a reference frame (x, y, z, $\alpha$, $\beta$, $\gamma$) that takes the end effector shaft through the trocar reference point.

In various embodiments, to determine the reference frame (x, y, z, $\alpha$, $\beta$, $\gamma$) that takes the distal end of the end effector shaft through the trocar reference point, a desired vector may be determined from the trocar reference point to a desired incremental point with respect to the distal end of the end effector shaft. In various embodiments, a current vector representing the current end effector shaft vector (i.e., a longitudinal axis of the end effector currently extending through the trocar) may be determined. In various embodiments, the in-plane rotation of the end effector may be determined using the desired vector and the current vector. In various embodiments, a reference frame may be determined from the transformation of the current end effector shaft vector using the in-plane rotation. In various embodiments, the frame may be converted into a desired coordinate system.

FIGS. 4A-4D shows a robotic arm system that is configured to follow a linear path while performing a laparoscopic surgery according to embodiments of the present disclosure. The robotic arm may be substantially similar to the robotic arm shown in FIG. 1 and may comprise an end effector 104 that is inserted into a trocar that was previously inserted into a keyhole incision in a body 108. In the examples shown in FIGS. 4A-4D, the distal end of the end effector 104 may follow a first linear path once inserted into the trocar from trocar reference point 202 to 206a and may then follow a second linear path (similar to the linear path illustrated in FIG. 2) defined by a vector 207 from a starting point 206a, through incremental points 206b-206e, before ending at a destination point 206f. Once inserted at the appropriate angle to reach the starting point 206a, the distal end of the end effector 104 may follow the linear path from point 206a to point 206f such that the end effector 104 shaft passes through the trocar reference point 202 at each incremental point 206b-206e. Projections 204a-204f represent the projection of the end effector 104 shaft through the trocar reference point to each incremental point 206a-206f. In various embodiments, the methods described herein may be similarly applied to each motion of the end effector, including, for example, the linear motion towards 206a, the linear motion from 206a to 206f, and the linear motion from 206f to another point outside of a subject's body.

Figure 4A:
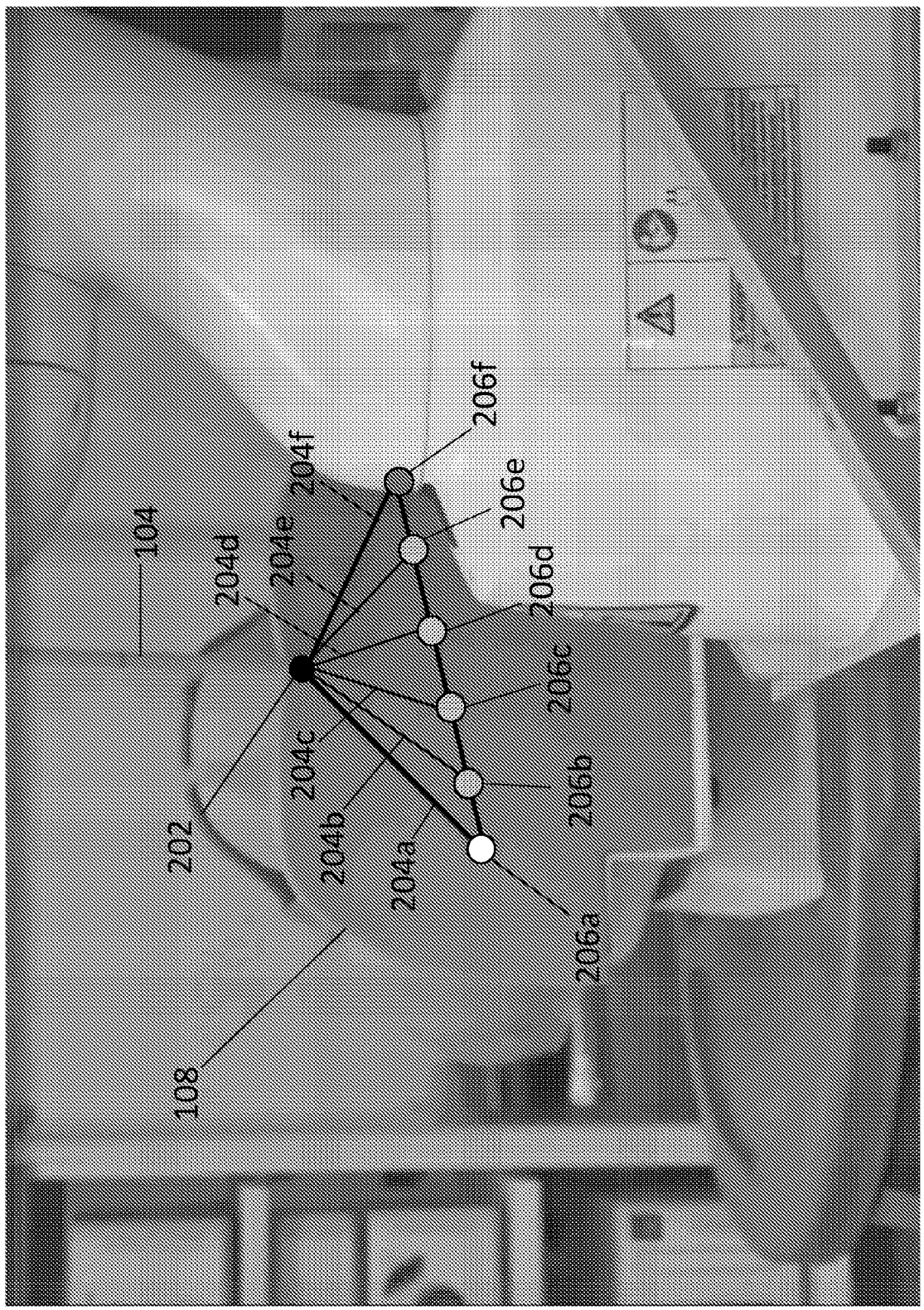
FIGS. 4A, 4B, 4C, and 4D schematically illustrate a robotic arm system configured to follow a linear path while performing a laparoscopic surgery, in accordance with some embodiments.
Figure 4B:
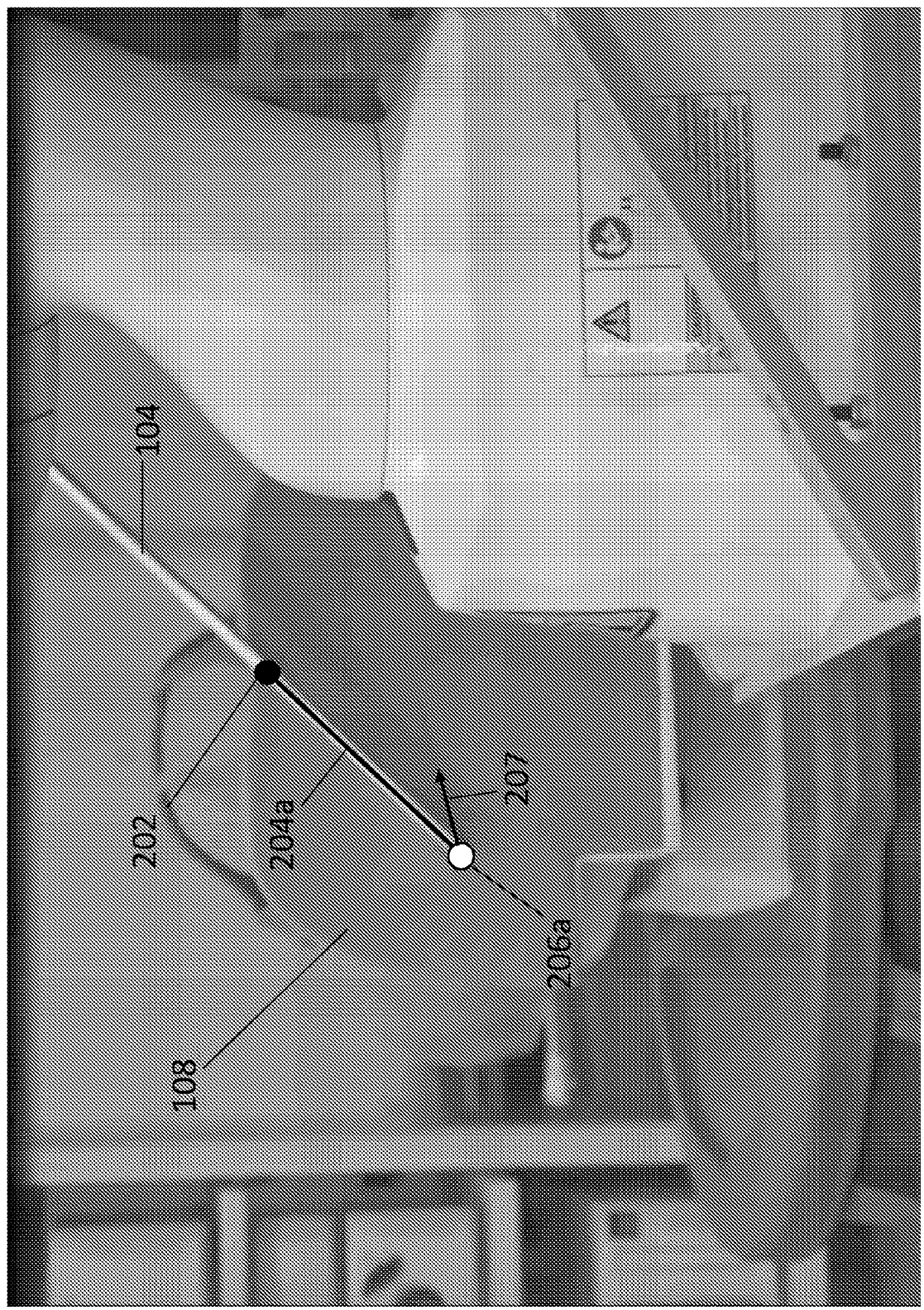

FIG. 4B shows the end effector 104 inserted into the trocar (previously inserted into the keyhole incision) such that the end effector 104 passes through the trocar reference point 202 and the distal end of the end effector 104 is located at the starting point 206a. The distal end of the end effector 104 may follow a linear path defined by the vector 207. The path defined by vector 207 may be broken, divided, or segmented (e.g., discretized) into incremental steps of one or more predetermined lengths as described above. The predetermined lengths between each of the plurality of points may be of a same length. Alternatively, the predetermined lengths between each of the plurality of points may be different lengths. In some cases, the one or more predetermined lengths may be at least about 1 nanometer, 1 micrometer, 1 millimeter, 1 centimeter, or more.

Figure 4C:
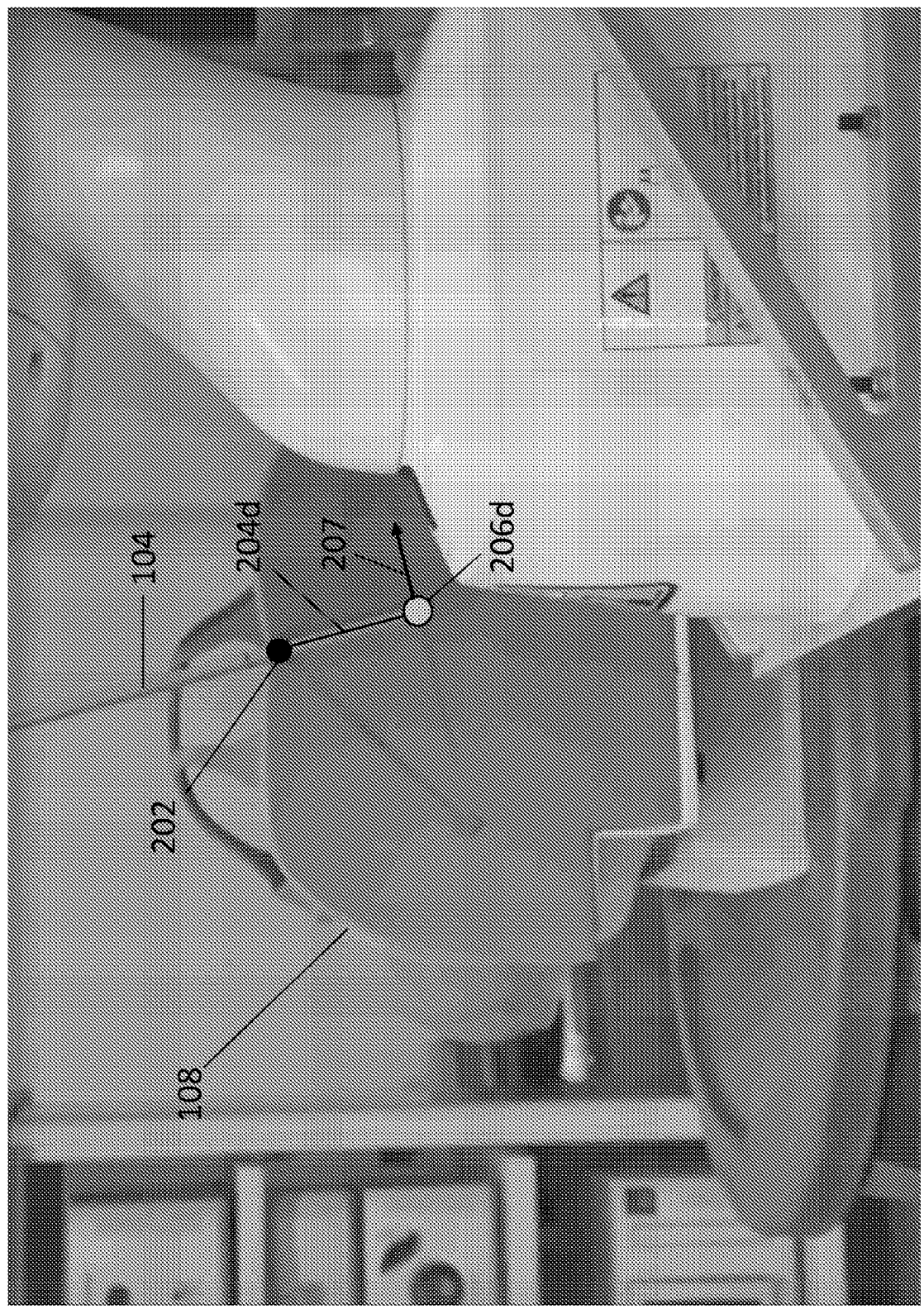
Figure 4D:
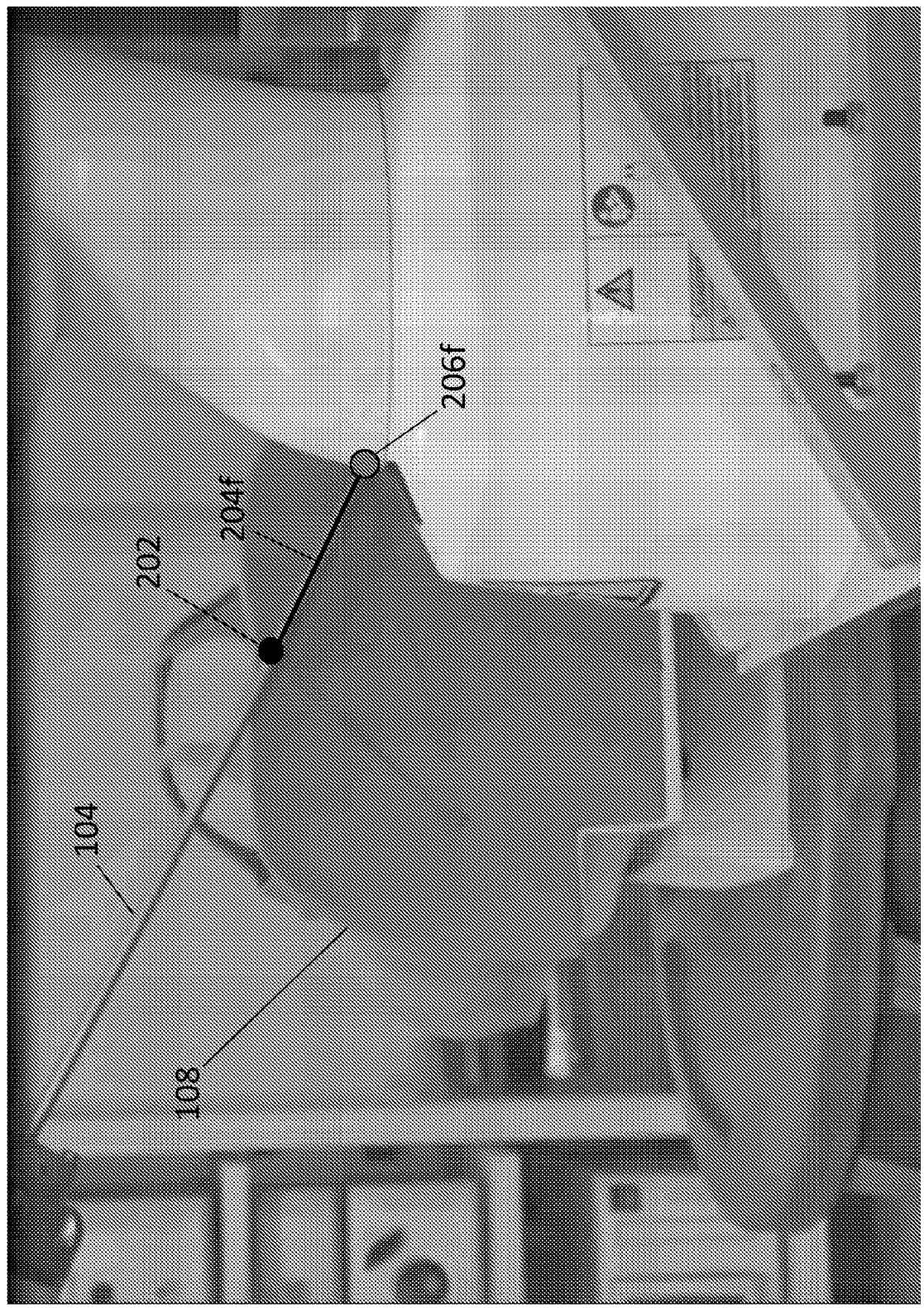

FIG. 4C shows a snapshot of the motion of the distal end of the end effector 104 at point 206d while following the linear path to the destination point 206f. As shown in FIG. 4C, the length of projection 204d may be shorter than the length of projection 204a (because the distance from the trocar reference point 202 to point 206d is shorter than the distance from the trocar reference point 202 to point 206a), and the end effector 104 shaft may continue to pass through the trocar reference point 202 while the distal end of the end effector follows the linear path. FIG. 4D shows a snapshot of the motion of the distal end of the end effector 104 at destination point 206f.

Figure 5A:
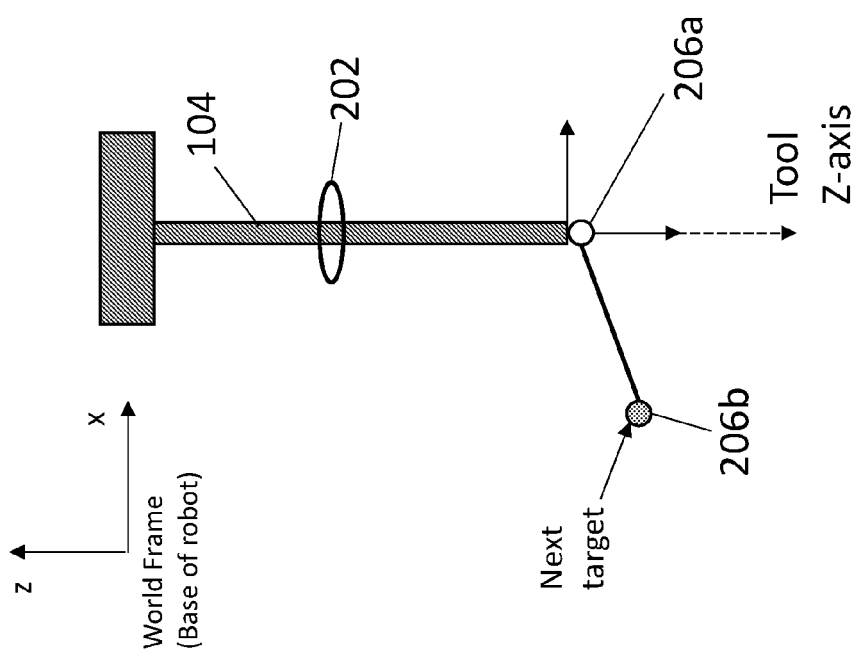
FIGS. 5A and 5B schematically illustrate a process for iteratively computing steps in a trocar-constrained path of an end effector, in accordance with some embodiments.
Figure 5B:
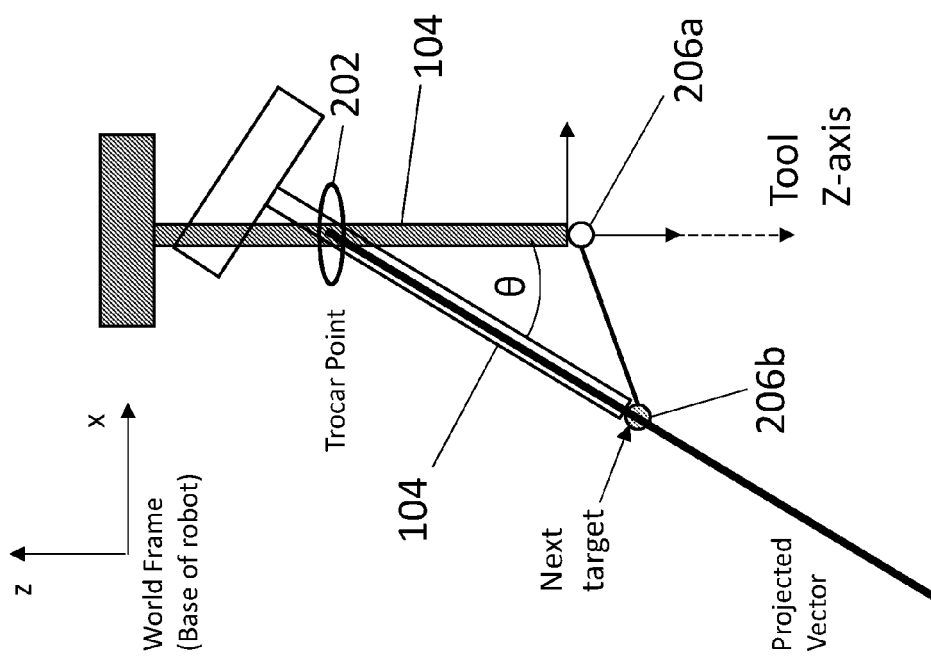

FIGS. 5A-5B illustrate a process for iteratively computing steps in a trocar-constrained path of an end effector according to embodiments of the present disclosure. When computing the path of the distal end of the end effector 104, a world frame of reference and an end effector frame of reference may be used. The world frame of reference may correspond to a frame of reference or a coordinate system in which the base of the robot is considered the origin. Certain variables used to compute an incremental next position of the trocar may include:

1. curTool, representing the current end effector tip location in the end effector frame (x,y,z);
2. trocTool, representing the trocar reference point location in end effector frame (x,y,z);
3. projVect, representing the projected vector from the trocar reference point to the next target position (x,y,z) of the end effector tip;
4. nexTarg, representing the location of the next incremental target position (x,y,z) of the end effector tip;
5. zTool, representing the vector that is the z-axis of the end effector (x,y,z) in the tool frame.

The current location of the end effector may be used as the starting point in the algorithm when the motion path is discretized. In various embodiments, the current location may be used as the origin (or reference frame) from which the other points are transformed to for the Rotation matrix equations described below. In various embodiments, the current end effector tip location may allow the trocar location and the next target location to be expressed with the current location of the end effector as the origin, thereby simplifying the calculations of one or more of the below equations.

In various embodiments, as shown below in Equation 1, a projected vector may be computed based on a difference in position between the next incremental target position and the trocar reference point location.

$$\text{projVect} = \text{nextTarg} - \text{trocTool} \quad \text{(Eqn. 1)}$$

As illustrated in FIG. 5B, an in-plane rotation may be computed between the z-axis of the trocar and the projected vector from the trocar reference point to the next target position of the distal end of the end effector. In various embodiments, the in-plane rotation may be represented as a rotation matrix between the z-axis of the trocar and the projected vector. The rotation matrix R may be computed based at least in part on a cross product of the trocar z-axis vector and the projected vector. The cross product of the trocar z-axis vector and the projected vector may be a vector v, as shown below in Equation 2.

$$v = z\text{Tool} \times \text{projVect} \quad \text{(Eqn. 2)}$$

As illustrated in FIG. 5B, an angle θ between the z-axis of the trocar and the projected vector may be computed, as shown below in Equation 3.

$$\theta = \cos^{-1} \frac{(z\text{Tool} \cdot \text{projVect})}{\|z\text{Tool}\| \|\text{projVect}\|} \quad \text{(Eqn. 3)}$$

In various embodiments, a cross product matrix may be determined based at least in part on the vector v corresponding to the cross product of the trocar z-axis vector and the projected vector computed from Equation 2, as shown below in Equation 4.

$$[v]_x \stackrel{\text{def}}{=} \begin{bmatrix} 0 & -v_3 & v_2 \\ v_3 & 0 & -v_1 \\ -v_2 & v_1 & 0 \end{bmatrix} \quad \text{(Eqn. 4)}$$

In various embodiments, a rotation matrix R may be computed based on the current end effector tip location in the tool frame, as shown below in Equation 5. The current end effector tip location may be transformed using the rotation matrix R to determine the rotation (in the tool frame) of the next target position. The translation of the current end effector tip location to the next target location may be determined from the position data (x, y, z) in the end effector frame. In various embodiments, the rotation matrix may be represented as a 4×4 matrix of [Rotation] [Translation], where I is the identity matrix.

$$R = I + v_x * \sin(\theta) + v_x^2 * (1 - \cos(\theta)) \quad \text{(Eqn. 5)}$$

In various embodiments, a homogeneous transformation H that combines rotation and displacement in a single matrix may be computed as shown below in Equations 6a and 6b:

$$H = \begin{bmatrix} R & d \\ 0 & 1 \end{bmatrix} \quad \text{(Eqn. 6a)}$$

$$H = \begin{bmatrix} n_x & s_x & a_x & d_x \\ n_y & s_y & a_y & d_y \\ n_z & s_z & a_z & d_z \\ 0 & 0 & 0 & 1 \end{bmatrix} \quad \text{(Eqn. 6b)}$$

In Equations 6a and 6b, the rotation may be represented by a 3×3 matrix which includes Euler angles (n, s, a), and the displacement may be represented by a 1×3 matrix which includes vector d.

The current end effector tip location may be transformed through matrix multiplication to determine the rotation of the next target position for the next incremental point. In various embodiments, the current end effector tip location, which can be represented as a 4×4 matrix of its current rotation and (x, y, z) position, may be multiplied by the rotation matrix R to compute the rotated point.

For example, the current end effector tip location may be represented as a 4×4 matrix of its current rotation and (x, y, z) position. The rotation matrix may also be represented as a 4×4 matrix (with a 1×4 column of 0, 0, 0, 1 representing no translation). The 4×4 rotation matrix may be multiplied by the 4×4 matrix of the current end effector tip position to compute a new 4×4 matrix including the rotated point. This new 4×4 matrix may include the position and/or orientation information required to move the end effector to the next point, and the (x, y, z) coordinates of the new 4×4 matrix may correspond to the (x, y, z) coordinates of the next target point. In various embodiments, this new 4×4 matrix may be transformed into the world reference frame (where the base of the robot is considered the origin) for commanding the robot.

In various embodiments, the transformation from end effector reference frame to the world frame may be derived based at least in part on the end effector dimensions, the position and/or orientation of the end effector relative to the robot arm, and the current joint locations of the robot. In various embodiments, this information may be used to determine one or more transformations from the end effector reference frame to the world frame through similar multiplication of the current 4×4 rotation matrix of the end effector by another 4×4 matrix corresponding to a position of the attachment point of the end effector to the robot arm. In various embodiments, another transformation may be performed from a first reference frame corresponding to the robot attachment point (or flange) to a second reference frame corresponding to the base of the robot, based at least in part on (i) the robot's dimensions and/or (ii) the relative positions and/or the relative orientations of the robot's joints.

In various embodiments, the position and/or orientation of the trocar may be determined based at least in part on the current configuration of the robotic arm (e.g., the positions and/or orientations of each of the joints of the robotic arm relative to the robotic arm) and the transformation of the rotation matrix from the tool frame into the world frame.

In various embodiments, the computational process implemented using Equations 1-5 may be repeated for each incremental step of a discretized motion path. In various embodiments, the process may be applied to a linear path, a curved path, or a path that comprises both linear and curved portions. In various embodiments, the frames (positions and orientations) may be splined together. In various embodiments, one or more incremental points may be splined together by instructing the robot to move continuously from one point to the next point such that the robot does not move the end effector to a first point and stop before moving to the next point (i.e., a second point) and stopping in a piecewise fashion. In various embodiments, the incremental points may be splined together to generate a motion plan where the points are reached in a smooth fashion as if the end effector is tracing the path. In various embodiments, the velocity and/or the acceleration of the robot may be managed. In various embodiments, the robotic arm or the end effector of the robotic arm may move at a constant linear or angular speed. In various embodiments, the incremental points of the end effector path may not or need not be splined together.

In various embodiments, any suitable tool having a straight shaft for insertion may be used as an end effector. In various embodiments, the end effector may comprise a rod with a grasper. For example, an Endo360 suturing tool may be used as an end effector. In various embodiments, the end effector may comprise one or more straight and/or curved portions. In various embodiments, the portion of the end effector that is inserted into the trocar may be substantially straight.

Figure 6:
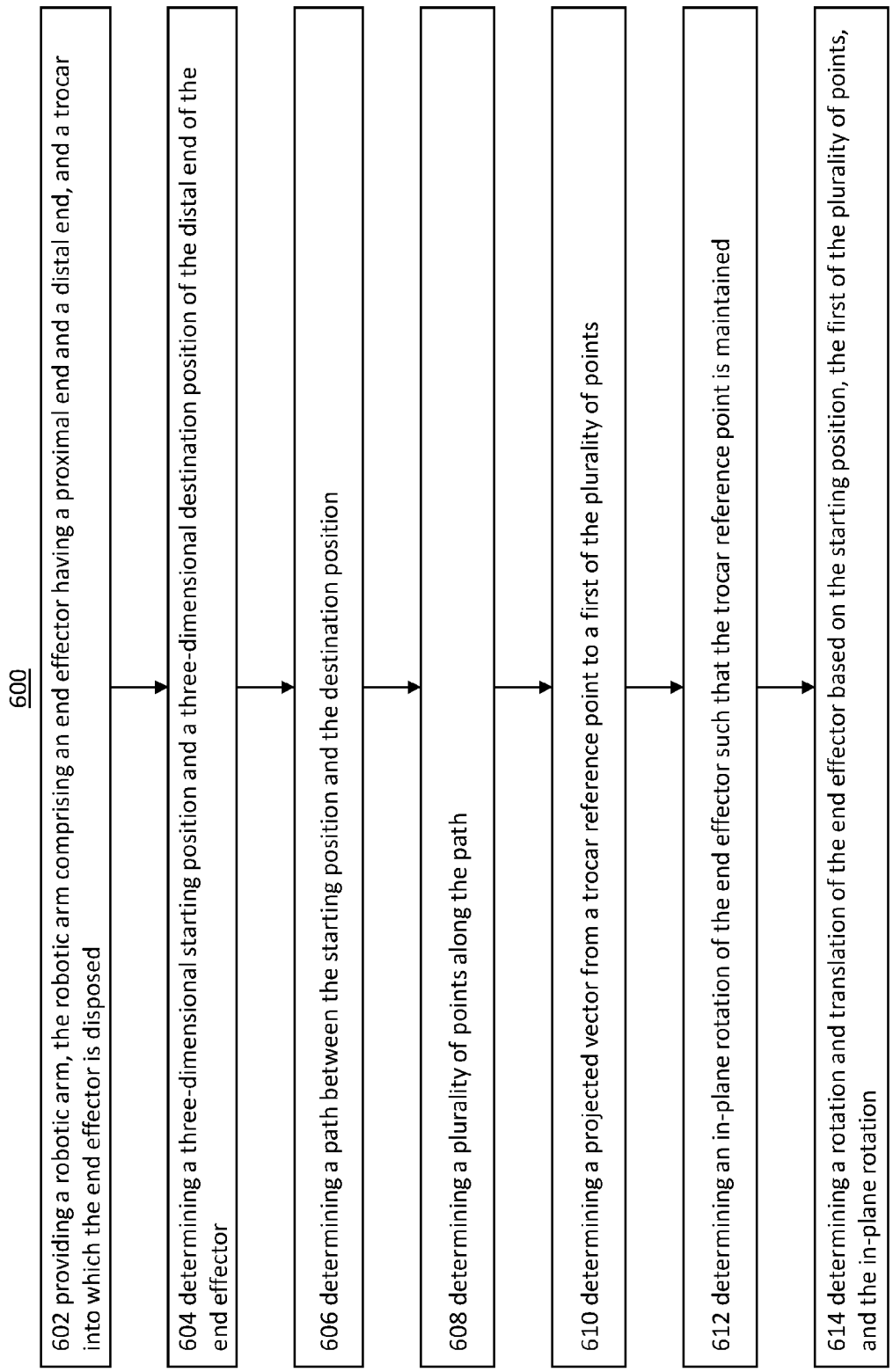
FIG. 6 schematically illustrates a flowchart of a method for determining a trocar-constrained path of an end effector, in accordance with some embodiments.

FIG. 6 illustrates a flowchart of a method 600 for determining a path and rotation of an end effector according to an embodiment of the present disclosure. At 602, a robotic arm may be provided. The robotic arm may comprise an end effector having a proximal end and a distal end. The end effector may be disposed within a trocar that is insertable in a keyhole incision in a subject's body. At 604, a three-dimensional starting position and a three-dimensional destination position of the distal end of the end effector may be determined. At 606, a path between the starting position and the destination position may be determined. At 608, a plurality of points along the path may be determined. At 610, a projected vector may be determined from a trocar reference point to a first point of the plurality of points. At 612, an in-plane rotation of the end effector may be determined such that the trocar reference point may be maintained. At 614, a rotation and/or a translation of the end effector may be determined based at least in part on the starting position, the first point of the plurality of points, and/or the in-plane rotation.

Figure 7:
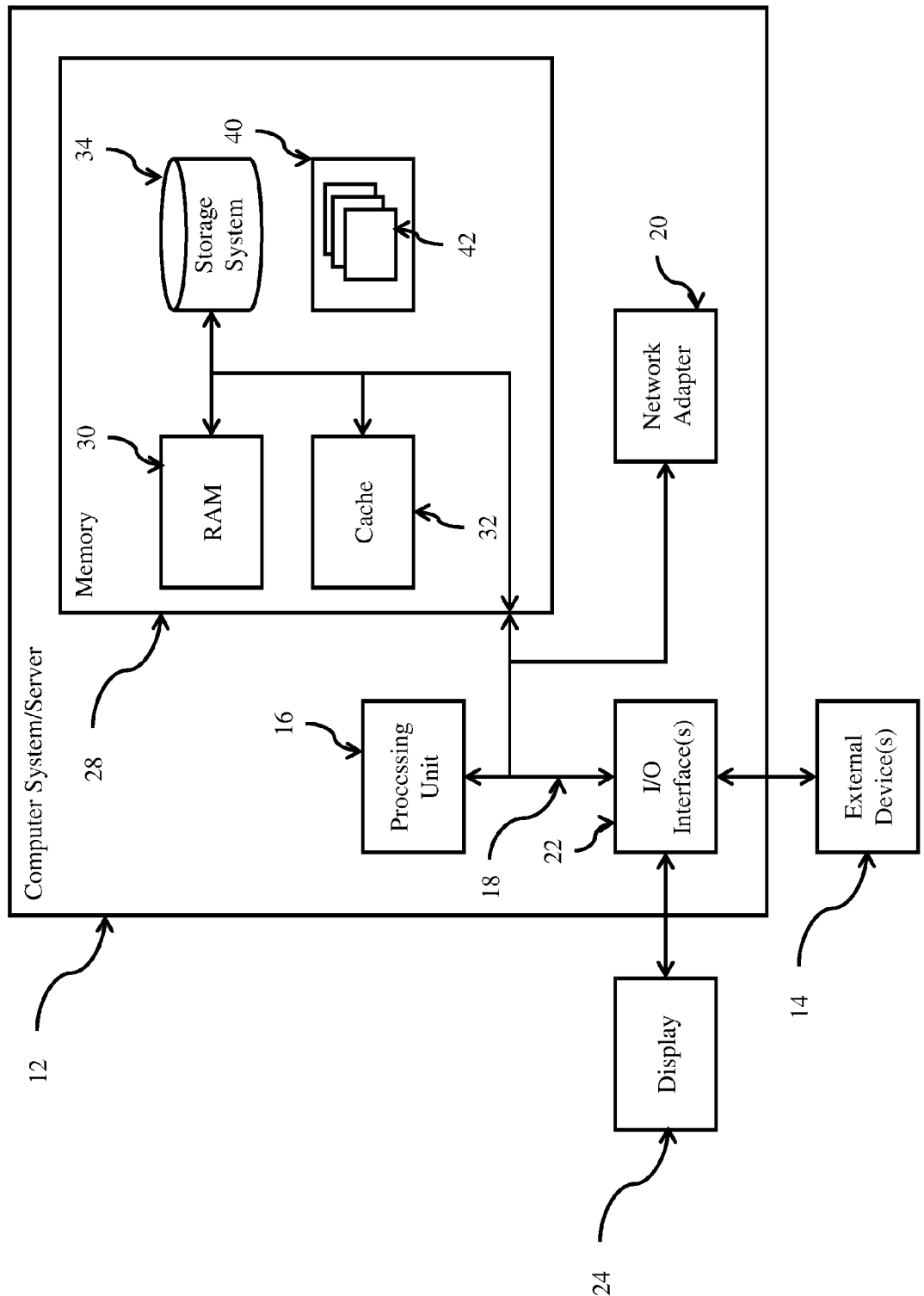
FIG. 7 schematically illustrates an exemplary computing node according to various embodiments of the present disclosure.

Referring now to FIG. 7, a schematic of an exemplary computing node is shown that may be used with the computer vision systems described herein. Computing node 10 is only one example of a suitable computing node and is not intended to suggest any limitation as to the scope of use or functionality of embodiments described herein. Regardless, computing node 10 is capable of being implemented and/or performing any of the functionality set forth hereinabove.

The computing node 10 may comprise a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 7, computer system/server 12 in computing node 10 is shown in the form of a general-purpose computing device. The components of computer system/server 12 may include, but are not limited to, one or more processors or processing units 16, a system memory 28, and a bus 18 coupling various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the disclosure.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

In other embodiments, the computer system/server may be connected to one or more cameras (e.g., digital cameras, light-field cameras) or other imaging/sensing devices (e.g., infrared cameras or sensors).

The present disclosure includes a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In various embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In various alternative implementations, the functions noted in the block may occur out of the order noted in the figures. For example, two blocks shown in succession may, in fact, be executed substantially concurrently, or the blocks may sometimes be executed in the reverse order, depending upon the functionality involved. Each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Computer Systems

Figure 8:
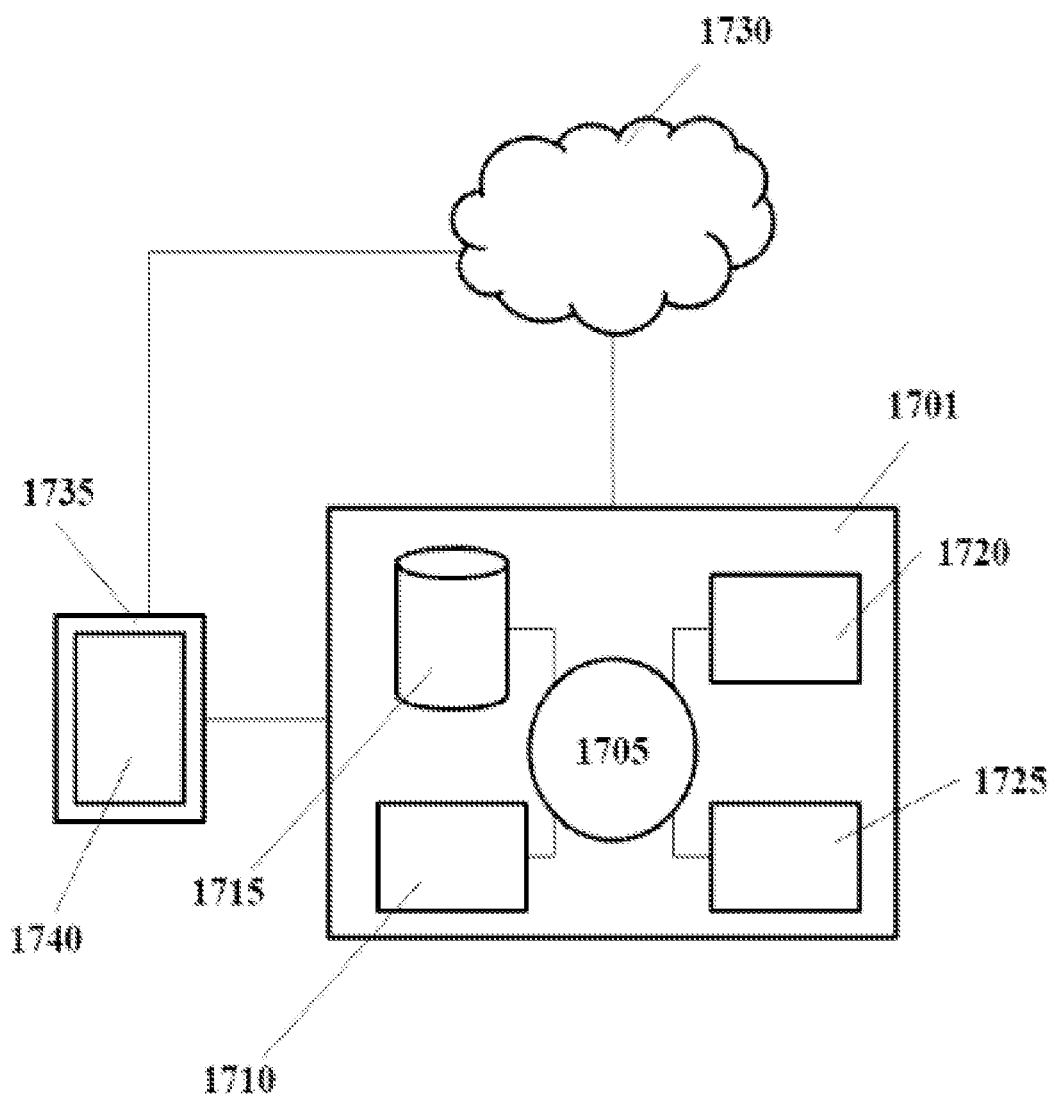
FIG. 8 schematically illustrates a computer system that is programmed or otherwise configured to implement methods provided herein.

In another aspect, the present disclosure provides computer systems that are programmed or otherwise configured to implement methods of the disclosure, e.g., any of the subject methods for medical imaging. FIG. 8 shows a computer system 1701 that is programmed or otherwise configured to implement a method for moving a robotic arm and/or an end effector of the robotic arm. The computer system 1701 may be configured to, for example, determine a set of motions to move the end effector from a starting position to a destination position, based at least in part on a trocar reference point. The computer system 1701 may be further configured to determine the starting position and the destination position of the distal end of the end effector, determine a path between the starting position and the destination position; and determine a plurality of points along the path. The computer system 1701 may be further configured to determine a projected vector from the trocar reference point to a first point of the plurality of points, determine an in-plane rotation of the end effector such that the trocar reference point is maintained, and determine a rotation and translation of the end effector based in part on the starting position, the first point of the plurality of points, and the in-plane rotation. The computer system 1701 may be further configured to transform the determined rotation and translation of the end effector from a first reference frame to a second reference frame. The computer system 1701 can be an electronic device of a user or a computer system that is remotely located with respect to the electronic device. The electronic device can be a mobile electronic device.

The computer system 1701 may include a central processing unit (CPU, also "processor" and "computer processor" herein) 1705, which can be a single core or multi core processor, or a plurality of processors for parallel processing. The computer system 1701 also includes memory or memory location 1710 (e.g., random-access memory, read-only memory, flash memory), electronic storage unit 1715 (e.g., hard disk), communication interface 1720 (e.g., network adapter) for communicating with one or more other systems, and peripheral devices 1725, such as cache, other memory, data storage and/or electronic display adapters. The memory 1710, storage unit 1715, interface 1720 and peripheral devices 1725 are in communication with the CPU 1705 through a communication bus (solid lines), such as a motherboard. The storage unit 1715 can be a data storage unit (or data repository) for storing data. The computer system 1701 can be operatively coupled to a computer network ("network") 1730 with the aid of the communication interface 1720. The network 1730 can be the Internet, an internet and/or extranet, or an intranet and/or extranet that is in communication with the Internet. The network 1730 in some cases is a telecommunication and/or data network. The network 1730 can include one or more computer servers, which can enable distributed computing, such as cloud computing. The network 1730, in some cases with the aid of the computer system 1701, can implement a peer-to-peer network, which may enable devices coupled to the computer system 1701 to behave as a client or a server.

The CPU 1705 can execute a sequence of machine-readable instructions, which can be embodied in a program or software. The instructions may be stored in a memory location, such as the memory 1710. The instructions can be directed to the CPU 1705, which can subsequently program or otherwise configure the CPU 1705 to implement methods of the present disclosure. Examples of operations performed by the CPU 1705 can include fetch, decode, execute, and writeback.

The CPU 1705 can be part of a circuit, such as an integrated circuit. One or more other components of the system 1701 can be included in the circuit. In some cases, the circuit is an application specific integrated circuit (ASIC).

The storage unit 1715 can store files, such as drivers, libraries and saved programs. The storage unit 1715 can store user data, e.g., user preferences and user programs. The computer system 1701 in some cases can include one or more additional data storage units that are located external to the computer system 1701 (e.g., on a remote server that is in communication with the computer system 1701 through an intranet or the Internet).

The computer system 1701 can communicate with one or more remote computer systems through the network 1730. For instance, the computer system 1701 can communicate with a remote computer system of a user (e.g., a healthcare provider, a surgical operator, a doctor, a nurse, an imaging technician, medical staff, etc.). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1701 via the network 1730.

Methods as described herein can be implemented by way of machine (e.g., computer processor) executable code stored on an electronic storage location of the computer system 1701, such as, for example, on the memory 1710 or electronic storage unit 1715. The machine executable or machine readable code can be provided in the form of software. During use, the code can be executed by the processor 1705. In some cases, the code can be retrieved from the storage unit 1715 and stored on the memory 1710 for ready access by the processor 1705. In some situations, the electronic storage unit 1715 can be precluded, and machine-executable instructions are stored on memory 1710.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1701, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media including, for example, optical or magnetic disks, or any storage devices in any computer(s) or the like, may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1701 can include or be in communication with an electronic display 1735 that comprises a user interface (UI) 1740 for providing, for example, a portal for a surgical operator to monitor or track a motion of a robotic arm and/or an end effector of the robotic arm. The portal may be provided through an application programming interface (API). A user or entity can also interact with various elements in the portal via the UI. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1705. The algorithm may be configured to determine a set of motions to move the end effector from a starting position to a destination position, based at least in part on a trocar reference point. The algorithm may be further configured to determine the starting position and the destination position of the distal end of the end effector, determine a path between the starting position and the destination position; and determine a plurality of points along the path. The algorithm may be further configured to determine a projected vector from the trocar reference point to a first point of the plurality of points, determine an in-plane rotation of the end effector such that the trocar reference point is maintained, and determine a rotation and translation of the end effector based in part on the starting position, the first point of the plurality of points, and the in-plane rotation. The algorithm may be further configured to transform the determined rotation and translation of the end effector from a first reference frame to a second reference frame.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method, comprising:
   (a) providing (i) a robotic arm including an end effector, (ii) a trocar through which the end effector is insertable, wherein the trocar includes a trocar reference point, and (iii) a processor; and
   (b) using the processor to (i) determine a starting position and a destination position of a distal end of the end effector, (ii) compute a path between the starting position and the destination position, (iii) identify a plurality of points along the path, (iv) generate a set of motions to move the distal end of the end effector from the starting position to the destination position, based at least in part on the trocar reference point, and (v) determine a projected vector from the trocar reference point to a first point of the plurality of points,
   wherein the set of motions includes an in-plane rotation of the end effector that maintains the trocar reference point during the in-plane rotation, and wherein the in-plane rotation is determined based at least in part on a rotation matrix, wherein the rotation matrix is computed as a function of a trocar z-axis vector and the projected vector.

2. The method of claim 1, wherein the end effector comprises a medical tool or an imaging device.

3. The method of claim 1, wherein the trocar reference point corresponds to a reference point that is located on the trocar.

4. The method of claim 3, wherein the reference point corresponds to a portion of the trocar that is located adjacent to an incision in a subject's body.

5. The method of claim 1, further comprising using the trocar reference point to compute a reference frame of the end effector.

6. The method of claim 1, further comprising using the trocar reference point to compute a relative position and a relative orientation of the end effector.

7. The method of claim 1, further comprising using the set of motions to adjust a position and an orientation of the distal end of the end effector to enable a medical operator to access one or more portions of a surgical scene while avoiding one or more obstacles in the surgical scene.

8. The method of claim 1, further comprising using the set of motions to adjust a position and an orientation of the distal end of the end effector to enable a medical operator to perform one or more steps of a surgical procedure while minimizing damage to a subject.

9. The method of claim 1, further comprising determining one or more rotations and one or more translations of the end effector to move the distal end of the end effector to the destination position, based at least in part on the starting position, the first point of the plurality of points, and the in-plane rotation of the end effector.

10. The method of claim 1, wherein the rotation matrix comprises a rotation portion corresponding to a rotational motion of the end effector and a translation portion corresponding to a translational motion of the end effector.

11. The method of claim 1, wherein the rotation matrix comprises an N×N matrix, wherein N is an integer greater than or equal to 3.

12. A method comprising:
   (a) providing (i) a robotic arm including an end effector, (ii) a trocar through which the end effector is insertable, wherein the trocar includes a trocar reference point, and (iii) a processor; and
   (b) using the processor to (i) determine a starting position and a destination position of a distal end of the end effector, (ii) compute a path between the starting position and the destination position, (iii) identify a plurality of points along the path, (iv) generate a set of motions to move the distal end of the end effector from the starting position to the destination position, based at least in part on the trocar reference point, and (v) determine a projected vector from the trocar reference point to a first point of the plurality of points,
   wherein the set of motions includes an in-plane rotation of the end effector that maintains the trocar reference point during the in-plane rotation, and wherein the in-plane rotation is determined based at least in part on an angle between the end effector and the projected vector.

13. The method of claim 12, wherein the angle between the end effector and the projected vector ranges from 0 degrees to about 45 degrees.

14. The method comprising:
(a) providing (i) a robotic arm including an end effector, (ii) a trocar through which the end effector is insertable, wherein the trocar includes a trocar reference point, and (iii) a processor; and
(b) using the processor to (i) determine a starting position and a destination position of a distal end of the end effector, (ii) compute a path between the starting position and the destination position, (iii) identify of plurality of points along the path, and (iv) generate a set of motions to move the distal end of the end effector from the starting position to the destination position, based at least in part on the trocar reference point,
wherein the set of motions includes an in-plane rotation of the end effector that maintains the trocar reference point during the in-plane rotation, and wherein the plurality of points along the path are determined by discretizing the path into a plurality of segments.

15. The method of claim 1, wherein the path comprises a linear portion defined by at least one vector.

16. The method of claim 1, wherein the path comprises a curved portion defined by a plurality of vectors.

17. A method comprising:
(a) providing (i) a robotic arm including an end effector, (ii) a trocar through which the end effector is insertable, wherein the trocar includes a trocar reference point, and (iii) a processor; and
(b) using the processor to (i) determine a starting position and a destination position of a distal end of the end effector, (ii) compute a path between the starting position and the destination position, (iii) identify a plurality of points along the path, (iv) generate a set of motions to move the distal end of the end effector from the starting position to the destination position, based at least in part on e trocar reference point, (v) determine a projected vector from the trocar reference point to a first point of the plurality of points, (vi) determine one or more rotations and one or more translations of the end effector to move the distal end of the end effector to the destination position, based at least in part on the starting position, the first point of the plurality of points, and an in-plane rotation of the end effector, and (vii) determine a set of transformations for the one or more rotations and the one or more translations of the end effector from a first reference frame to a second reference frames,
wherein the set of motions includes the in-plane rotation of the end effector that maintains the trocar reference point during the in-plane rotation.

18. The method of claim 17, wherein the first reference frame is defined relative to the end effector and the second reference frame is defined relative to the robotic arm.

* * * * *